US009603851B2

(12) United States Patent
Klein et al.

(10) Patent No.: US 9,603,851 B2
(45) Date of Patent: Mar. 28, 2017

(54) COMBINATION THERAPY

(71) Applicant: Boehringer Ingelheim International GmbH, Ingelheim am Rhein (DE)

(72) Inventors: Thomas Klein, Radolfzell (DE); Rolf Grempler, Birkenhard/Warthausen (DE); Michael Mark, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/873,579

(22) Filed: Oct. 2, 2015

(65) Prior Publication Data

US 2016/0038500 A1 Feb. 11, 2016

Related U.S. Application Data

(63) Continuation of application No. 13/695,492, filed as application No. PCT/EP2011/057256 on May 5, 2011, now Pat. No. 9,186,392.

(30) Foreign Application Priority Data

May 5, 2010 (EP) .................................. 10162036
Feb. 21, 2011 (EP) .................................. 11155154

(51) Int. Cl.
| | | |
|---|---|---|
| A61K 31/00 | (2006.01) |
| A61K 31/522 | (2006.01) |
| A61K 38/00 | (2006.01) |
| A61P 3/04 | (2006.01) |
| A61P 3/10 | (2006.01) |
| A61K 38/26 | (2006.01) |
| A61K 45/06 | (2006.01) |
| A61K 38/22 | (2006.01) |

(52) U.S. Cl.
CPC ............ *A61K 31/522* (2013.01); *A61K 31/00* (2013.01); *A61K 38/2278* (2013.01); *A61K 38/26* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,056,046 A | 9/1936 | Fourneau |
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |
| 5,051,509 A | 9/1991 | Nagano et al. |
| 5,051,517 A | 9/1991 | Findeisen et al. |
| 5,084,460 A | 1/1992 | Munson, Jr. et al. |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.
Ferry, Robert Jr., "Diabetes Causes." eMedicine Health, MedicineNet.com, 2013, Retrieved from internet on Aug. 22, 2013, http://www.onhealth.com/diabetes_health/page3.htm#diabetes_causes.
Florez, J. et al. "TCF7L2 Polymorphisms and Progression to Diabetes in the Diabetes Prevention Program." The New England Journal of Medicine, 2006, vol. 355, No. 3, pp. 241-250.
Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.
Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.
Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.
Fukushima et al., Drug for Treating Type II Diabetes (6), "action-mechanism of DPP-IV inhibitor and the availability thereof" Mebio, 2009, vol. 26, No. 8, p. 50-58.

(Continued)

*Primary Examiner* — Julie Ha
*Assistant Examiner* — Kristina M Hellman
(74) *Attorney, Agent, or Firm* — Michael P. Morris; David L. Kershner

(57) ABSTRACT

The present invention relates to methods for treating and/or preventing metabolic diseases comprising the combined administration of a GLP-1 receptor agonist and a DPP-4 inhibitor.

2 Claims, 4 Drawing Sheets

(56) References Cited

U.S. PATENT DOCUMENTS

| | | |
|---|---|---|
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,200,958 B1 | 3/2001 | Odaka et al. |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,448,323 B1 | 9/2002 | Jordan et al. |
| 6,548,481 B1 | 4/2003 | Demuth et al. |
| 6,579,868 B1 | 6/2003 | Asano et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,890,898 B2 | 5/2005 | Bachovchin et al. |
| 6,995,183 B2 | 2/2006 | Hamann et al. |
| 7,034,039 B2 | 4/2006 | Oi et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,220,750 B2 | 5/2007 | Himmelsbach et al. |
| 7,235,538 B2 | 6/2007 | Kanstrup et al. |
| 7,247,478 B2 | 7/2007 | Eberhardt et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,407,995 B2 | 8/2008 | Ok et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,338,450 B2 | 12/2012 | Arora et al. |
| 8,455,435 B2 | 6/2013 | Franz et al. |
| 8,513,264 B2 | 8/2013 | Mark et al. |
| 8,541,450 B2 | 9/2013 | Pfrengle et al. |
| 8,637,530 B2 | 1/2014 | Pfrengle et al. |
| 8,664,232 B2 | 3/2014 | Himmelsbach et al. |
| 8,673,927 B2 | 3/2014 | Dugi et al. |
| 8,679,520 B2 | 3/2014 | Horres et al. |
| 8,697,868 B2 | 4/2014 | Himmelsbach et al. |
| 8,785,455 B2 | 7/2014 | Hotter et al. |
| 8,846,695 B2 | 9/2014 | Dugi |
| 8,853,156 B2 | 10/2014 | Dugi et al. |
| 8,865,729 B2 | 10/2014 | Sieger et al. |
| 8,883,800 B2 | 11/2014 | Pfrengle et al. |
| 8,883,805 B2 | 11/2014 | Pfrengle et al. |
| 8,962,636 B2 | 2/2015 | Pfrengle et al. |
| 9,034,883 B2 | 5/2015 | Klein et al. |
| 9,108,964 B2 | 8/2015 | Himmelsbach et al. |
| 9,149,478 B2 | 10/2015 | Klein et al. |
| 9,155,705 B2 | 10/2015 | Friedl et al. |
| 9,173,859 B2 | 11/2015 | Dugi et al. |
| 9,186,392 B2 | 11/2015 | Klein et al. |
| 9,199,998 B2 | 12/2015 | Pfrengle et al. |
| 9,212,183 B2 | 12/2015 | Sieger et al. |
| 9,266,888 B2 | 2/2016 | Sieger et al. |
| 9,321,791 B2 | 4/2016 | Himmelsbach et al. |
| 9,415,016 B2 | 8/2016 | Friedl et al. |
| 9,457,029 B2 | 10/2016 | Dugi et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0160047 A1 | 10/2002 | Hussain et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0040490 A1 | 2/2003 | Sugiyama et al. |
| 2003/0078269 A1 | 4/2003 | Pearson et al. |
| 2003/0100563 A1 | 5/2003 | Edmondson et al. |
| 2003/0104053 A1 | 6/2003 | Gusler et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0153509 A1 | 8/2003 | Bachovchin et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0037883 A1 | 2/2004 | Zhou et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152659 A1 | 8/2004 | Matsuoka et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt et al. |
| 2005/0027012 A1 | 2/2005 | Kohlrausch |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach et al. |
| 2005/0143377 A1 | 6/2005 | Himmelsbach et al. |

(56) References Cited

U.S. PATENT DOCUMENTS

| | | |
|---|---|---|
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0034922 A1 | 2/2006 | Cheng et al. |
| 2006/0039968 A1 | 2/2006 | Manikandan et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0173452 A1 | 7/2007 | DiMarchi et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0254944 A1 | 11/2007 | Hughes |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0234291 A1 | 9/2008 | Francois et al. |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0033177 A1 | 2/2010 | Ochi et al. |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2010/0317575 A1 | 12/2010 | Pinnetti et al. |
| 2011/0009391 A1 | 1/2011 | Braun et al. |
| 2011/0028391 A1 | 2/2011 | Holst et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0064887 A1 | 3/2013 | Ito et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |
| 2013/0303554 A1 | 11/2013 | Klein et al. |
| 2013/0315975 A1 | 11/2013 | Klein et al. |
| 2013/0317046 A1 | 11/2013 | Johansen |
| 2013/0324463 A1 | 12/2013 | Klein et al. |
| 2014/0100236 A1 | 4/2014 | Busl et al. |
| 2014/0274889 A1 | 9/2014 | Johansen et al. |
| 2014/0343014 A1 | 11/2014 | Klein et al. |
| 2014/0371243 A1 | 12/2014 | Klein et al. |
| 2015/0196565 A1 | 7/2015 | Klein et al. |
| 2015/0246045 A1 | 9/2015 | Klein et al. |
| 2015/0265538 A1 | 9/2015 | Balthes et al. |
| 2016/0082011 A1 | 3/2016 | Klein et al. |
| 2016/0106677 A1 | 4/2016 | Boeck et al. |
| 2016/0310435 A1 | 10/2016 | Friedl et al. |

FOREIGN PATENT DOCUMENTS

| | | |
|---|---|---|
| CA | 1123437 A1 | 5/1982 |
| CA | 2136288 A1 | 5/1995 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |

(56) References Cited

FOREIGN PATENT DOCUMENTS

| | | |
|---|---|---|
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2599419 A1 | 11/2006 |
| CA | 2651019 A1 | 11/2007 |
| CA | 2651089 A1 | 11/2007 |
| CN | 101234105 A | 8/2008 |
| DE | 2205815 A1 | 8/1973 |
| DE | 2758025 A1 | 7/1979 |
| DE | 19705233 A1 | 8/1998 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0638567 A1 | 2/1995 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| EP | 2166007 A1 | 3/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2001292388 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2004250336 A | 9/2004 |
| JP | 2006045156 A | 2/2006 |
| JP | 2010053576 A | 3/2010 |
| JP | 2010070576 A | 4/2010 |
| JP | 2010524580 A | 7/2010 |
| KR | 20070111099 A | 11/2007 |
| WO | 8706941 A1 | 11/1987 |
| WO | 9107945 A1 | 6/1991 |
| WO | 9205175 A1 | 4/1992 |
| WO | 9219227 A2 | 11/1992 |
| WO | 9402150 A1 | 2/1994 |
| WO | 9403456 A1 | 2/1994 |
| WO | 9532178 A1 | 11/1995 |
| WO | 9609045 A1 | 3/1996 |
| WO | 9611917 A1 | 4/1996 |
| WO | 9636638 A1 | 11/1996 |
| WO | 9718814 A1 | 5/1997 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 | 3/1998 |
| WO | 9818770 A1 | 5/1998 |
| WO | 9822464 A1 | 5/1998 |
| WO | 9828007 A1 | 7/1998 |
| WO | 9840069 A2 | 9/1998 |
| WO | 9846082 A1 | 10/1998 |
| WO | 9856406 A1 | 12/1998 |
| WO | 9929695 A1 | 6/1999 |
| WO | 9938501 A2 | 8/1999 |
| WO | 9950248 A1 | 10/1999 |
| WO | 9956561 A1 | 11/1999 |
| WO | 9967279 A1 | 12/1999 |
| WO | 0034241 A1 | 6/2000 |
| WO | 0069464 A1 | 11/2000 |
| WO | 0072799 A2 | 12/2000 |
| WO | 0073307 A2 | 12/2000 |
| WO | 0078735 A1 | 12/2000 |
| WO | 0107441 A1 | 2/2001 |
| WO | 0132158 A2 | 5/2001 |
| WO | 0140180 A2 | 6/2001 |
| WO | 0147514 A1 | 7/2001 |
| WO | 0151919 | 7/2001 |
| WO | 0152825 | 7/2001 |
| WO | 0152852 A1 | 7/2001 |
| WO | 0166548 A1 | 9/2001 |
| WO | 0168603 | 9/2001 |
| WO | 0168646 A1 | 9/2001 |
| WO | 0172290 A2 | 10/2001 |
| WO | 0177110 A1 | 10/2001 |
| WO | 0196301 A1 | 12/2001 |
| WO | 0197808 A1 | 12/2001 |
| WO | 0202560 A2 | 1/2002 |
| WO | 0214271 A1 | 2/2002 |
| WO | 0224698 A1 | 3/2002 |
| WO | 02053516 A2 | 7/2002 |
| WO | 02068420 A1 | 9/2002 |
| WO | 03000241 A2 | 1/2003 |
| WO | 03000250 | 1/2003 |
| WO | 03002531 A2 | 1/2003 |
| WO | 03002553 A2 | 1/2003 |
| WO | 03004496 A1 | 1/2003 |
| WO | 03024965 A2 | 3/2003 |
| WO | 03033686 A2 | 4/2003 |
| WO | 03034944 A1 | 5/2003 |
| WO | 03035177 A2 | 5/2003 |
| WO | 03037327 A1 | 5/2003 |
| WO | 03053929 A1 | 7/2003 |
| WO | 03055881 A1 | 7/2003 |
| WO | 03057200 A2 | 7/2003 |
| WO | 03059327 | 7/2003 |
| WO | 03064454 A1 | 8/2003 |
| WO | 03074500 A2 | 9/2003 |
| WO | 03088900 A2 | 10/2003 |
| WO | 03094909 A2 | 11/2003 |
| WO | 03099279 A1 | 12/2003 |
| WO | 03099836 A1 | 12/2003 |

(56) References Cited

FOREIGN PATENT DOCUMENTS

| | | |
|---|---|---|
| WO | 03104229 A1 | 12/2003 |
| WO | 03106428 A1 | 12/2003 |
| WO | 2004002924 A1 | 1/2004 |
| WO | 2004011416 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007137 A2 | 1/2005 |
| WO | 2005007647 A1 | 1/2005 |
| WO | 2005007658 A2 | 1/2005 |
| WO | 2005012288 A1 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006078593 A2 | 7/2006 |
| WO | 2006083491 A2 | 8/2006 |
| WO | 2006116157 | 11/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 2007033350 A1 | 3/2007 |
| WO | 2007035355 A2 | 3/2007 |
| WO | 2007035665 A1 | 3/2007 |
| WO | 2007041053 A2 | 4/2007 |
| WO | 2007050485 A2 | 5/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007136151 A1 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092124 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010140111 A1 | 12/2010 |
| WO | 2010147768 A1 | 12/2010 |
| WO | 2011011541 A1 | 1/2011 |
| WO | 2011039337 A1 | 4/2011 |
| WO | 2011039367 A1 | 4/2011 |
| WO | 2011064352 A1 | 6/2011 |
| WO | 2011113947 A1 | 9/2011 |
| WO | 2011138380 A1 | 11/2011 |
| WO | 2011138421 A1 | 11/2011 |
| WO | 2011161161 A1 | 12/2011 |
| WO | 2011163206 A2 | 12/2011 |
| WO | 2012031124 A2 | 3/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012120040 A1 | 9/2012 |

(56) References Cited

FOREIGN PATENT DOCUMENTS

| | | | |
|---|---|---|---|
| WO | 2013098372 A1 | 7/2013 |
| WO | 2013103629 A1 | 7/2013 |
| WO | 2013131967 A1 | 9/2013 |
| WO | 2013171167 A1 | 11/2013 |
| WO | 2013174768 A1 | 11/2013 |
| WO | 2013179307 A2 | 12/2013 |

OTHER PUBLICATIONS

Gallwitz, B. "Sitagliptin with Metformin: Profile of a Combination for the Treatment of Type 2 Diabetes". Drugs of Today, Oct. 2007, 43(10), p. 681-689.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Gallwitz, B. et al., "Saxagliptin, a dipeptidyl peptidase IV inhibitor for the treatment of type 2 diabetes". Idrugs, vol. 11, No. 12, Dec. 2008, p. 906-917.
Gallwitz, B. et al., DPP IV inhibitors for the Treatment of Type 2 Diabetes; Diabetes Frontier (2007) vol. 18, No. 6 pp. 636-642.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Gennaro, Alfonso R. Remington Farmacia, 2003, Spanish copy: p. 828, English copy: pp. 711-712, Preformulation, Chapter 38.
Gennaro, Alfonso R., Remington Farmacia, 19th Edition, Spanish copy, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Gennaro, Alfonso; Remington: The Science and Practice of Pharmacy, Twentieth Edition, 2000, Chapter 45, pp. 860-869.
Giron, D.; Thermal Analysis and Calorimetric Methods in the Characterisation of Polymorphs and Solvates; Thermochimica Acta (1995) vol. 248 pp. 1-59.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.
Gomez-Perez, et al, "Insulin Therapy:current alternatives", Arch. Med.Res. 36: p. 258-272 (2005).
Graefe-Mody et al., "The novel DPP-4 inhibitor BI 1356 (proposed tradename Ondero) and Metformin can be Safely Co-administered Without Dose Adjustment." Poster No. 553-P ADA Jun. 6-10, 2008, San Francisco http://professional.diabetes.org/content/posters/2008/p553-p.pdf.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
"Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W, et al., "Protection for the Amino Group". Protective Groups in Organic Synthesis, 3rd edition, 1999, p. 494-653.
Greischel, et al., Drug Metabolism and Deposition, "The Dipeptidyl Peptidase-4 Inhibitor Linagliptin Exhibits Time- and Dpse-Dependent Localization in Kidney, Liver, and Intestine after Intravenous Dosing: Results from High Resolution Autoradiography in Rats", 2010, vol. 38, No. 9, p. 1443-1448.

Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct. 2012. <http://www.abstractsonline.com/Plan/ViewAbstract.aspx?sKey=0b0017b9-9e90-4695-b9af-b6870e96a921&cKey=421edb9c-b940-40f0-b282-8e61245561d5&mKey=2dbfcaf7-1539-42d5-8dda-0a94abb089e8>.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Gupta, V. et al., "Choosing a Gliptin." Indian Journal of Endocrinology and Metabolism, 2011, vol. 15, No. 4, pp. 298-308.
Gwaltney, S. "Medicinal Chemistry Approaches to the Inhibition of Dipeptidyl Peptidase IV", Current Topics in Medicinal Chemistry, 2008, 8, p. 1545-1552.
Hainer, Vojtech MD, PhD "Comparative Efficiency and Safety of Pharmacological Approaches to the Management of Obesity." Diabetes Care, 2011, vol. 34, Suppl. 2, pp. S349-S354.
Halimi, et al. "Combination treatment in the management of type 2 diabetes focus on vildagliptin and metformin as a single tablet", Vascualr Health and Risk Management, 2008, 4(3) p. 481-492.
Haluzik, M. et al., "Renal Effects of DPP-4 Inhibitors: A Focus on Microalbuminuria." International Journal of Endocrinology, 2013, vol. 35, No. 6, pp. 1-7.
Hammouda, Y. et al., "Lactose-induced Discoloration of Amino Drugs in Solid Dosage Form." Die Pharmazie, 1971, vol. 26, p. 181.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Hashida, Mitsuru, "Strategies for designing and developing oral administration formulations." Yakuji-Jiho, Inc., 1995, pp. 50-51.
Hayashi, Michio., "Recipe for Oral Hypoglycemic Agents to Pathological Condition" Pharmacy (2006) vol. 57, No. 9 pp. 2735-2739.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
He, Y.L. et al., "The influence of hepatic imparirment on the pharmacokinetics f the dipeptidyl peptidase IV (DPP-4) inhibitor vildagliptin" European Journal of Clinical Pharmacology, vol. 63, No. 7, May 8, 2007, p. 677-686.
Headland, K. et al., "The Effect of Combination Linagliptin and Voglibose on Glucose Control and Body Weight." 73rd Annual Meeting Science Session, ADA, Chicago, Jun. 21, 2013.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus

(56) References Cited

OTHER PUBLICATIONS

Inadequately Controlled on Glimepiride Alone or on Glimepiride and Metformin". Diabetes, Obesity and Metabolism (2007) vol. 9, No. 5 pp. 733-745.
Hilfiker, R. et al., "Relevance of Solid-state Properties for Pharmaceutical Products." Polymorphism in the Pharmaceutical Industry, 2006, Chapter 1, pp. 1-19.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Chemical Abstracts Service, Database Accession Number No. RN 668270-12-01, 2004, "1H-Purine-2,6-dione, 8-[(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Cheon, et al., Biochemical Pharmacology, "Inhibition of dipeptidyl IV by novel inhibitors with pyrazolidine scaffold", 2005, vol. 70, p. 22-29.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Clinical Trial NCT00622284 (published online at clinicaltrials.gov on Feb. 22, 2008).
Clinical Trials, No. NCT00309608, "Efficacy and Safety of BI 1356 BS in Combination with Metformin in Patients With type2 Diabetes" 2009, pp. 1-3.
Clinical Trials, No. NCT00622284, "Efficacy and Safety of BI 1356 in combination with metformin in patients with type 2 diabetes" 2012, pp. 1-5.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009].
Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of Bi 1356 Plus Metformin in Type 2 Diabetes, Factorial Design". Clinical Trials. gov archive. A Service of the U.S> National Institutes of Health. Nov. 24, 2008, p. 1-3. http://clinicaltrials.gov/archive/NCT00798161/2008_11_24.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Cotton, M.L. et al., "L-649,923—The selection of an appropriate salt form and preparation of a stable oral formulation." International Journal of Pharmaceutics, 1994, vol. 109, Issue 3, pp. 237-249.
Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.
Crowe, E. et al., "Early identification and management of chronic kidney disease: summary of NICE guidance." British Medical Journal, 2008, vol. 337, pp. 812-815.
Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.
Dave, Rutesh H. "Overview of pharmaceutical excipients used in tablets and capsules." Drug Topics, Oct. 24, 2008.
Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.
Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.
Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.
Deacon, Carolyn F. et al. "Linaglipitn, a xanthine-based dipeptidyl peptidase-4 inhibitor with an unusual profile for the treatment of type 2 diabetes" Expert Opin. Investig. Drugs (2010) 19(1): 133-140.
Definition of "prevent", e-dictionary, Aug. 15, 2013, http://dictionary.reference.com/browse/prevent.
DeMeester, I. et al.; "CD26, let it cut or cut it down", Review: Immunology Today; Aug. 1999, vol. 20, No. 8 pp. 367-375.
Demuth, H-U. et al., "Type 2 diabetes—Therapy with dipeptidyl peptidase IV inhibitors". Biochimica et Biophysica Acta, vol. 1751(1), 2005, p. 33-44.
Diabetes Frontier, 2007, vol. 18, No. 2, p. 145-148.
Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.
Diabetesincontrol.com "EASD: Eucreas, a Combination of Galvus and Metformin, Recommended for Approval." Diabetes in Control.com, Sep. 25, 2007, Retrieved from internet on Nov. 30, 2012, http://www.diabetesincontrol.com/articles/53-diabetes-news/5145.
Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.

(56) References Cited

OTHER PUBLICATIONS

Drucker, Daniel J., "Dipeptidyl Peptidase-4 Inhibition and the Treatment of Type 2 Diabetes." Diabetes Care, 2007, vol. 30, No. 6, pp. 1335-1343.
Drucker, et al.., The incretin system:glucagon-like peptide-1 receptor agonists and dipeptidyl peptidase-4 inhibitors in type 2 diabetes. Lancet, 2006, 368: 1696-705.
Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.
Dunitz, J. et al., "Disappearing Polymorphs." Acc. Chem. Res. 1995, vol. 28, No. 4, pp. 193-200.
Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.
Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.
Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.
Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.
EMEA: European Medicines Agency, ICH Topic E4, "Dose Response Information to Support Drug Registration." 1994, pp. 1-10.
eMedicine Health, "Diabetes Causes." Retrieved from internet on Aug. 22, 2013. <http://www.onhealth.com/diabetes_health/page3.htm#diabetes_causes>.
Eucreas Scientific Discussion, 2007, p. 1-27, www.emea.europa.eu/humandocs/PD/Fs/EPAR/eucreas/H-807-en6.pdf, Anonymous.
Eyjolfsson, Reynir "Lisinopril-Lactose Incompatibility." Drug Development and Industrial Pharmacy, 1998, vol. 24, No. 8, pp. 797-798.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Zejc, Alfred, et al; "Badania Nad Piperazynowymi Pochodnymi Dwumetyloksantyn" Acta Polon Pharm, XXXV (1976) Nr. 4 pp. 417-421.
Zhimei, Xiao et al., "Study progression of oral drugs for treatment of type II diabetes." Drug Evaluation, 2004, vol. 1 No. 2, pp. 138-143.
Zhong, Qing et al; "Glucose-dependent insulinotropic peptide stimulates proliferation and TGF-? release from MG-63 cells," Peptides 24 (2003) 611-616.
Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.
Zimdahl, H. et al., "Influence of TCF7L2 gene variants on the therapeutic response to the dipeptidylpeptidase-4 inhibitor linagliptin." Diabetologia, 2014, vol. 57, pp. 1869-1875.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Abstract in English for German DE10109021, 2002.
Abstract in English for German DE2205815, 1972.
Abstract in English for German EP0023032, 1981.
Abstract in English for JP 2002/348279, Dec. 4, 2002.
Abstract in English for JP 2003/286287, Oct. 10, 2003.
Abstract in English, for KR20070111099, Nov. 11, 2007.
Adebowale, K.O. et al., "Modification and properties of African yam bean (*Sphenostylis stenocarpa* Hochst. Ex A. Rich.) Harms starch I: Heat moisture treatments and annealing." Food Hydrocolloids, 2009, vol. 23, No. 7, pp. 1947-1957.
Ahren, Bo "Novel combination treatment of type 2 diabetes DPP-4 inhibition + metformin." Vascular Health and Risk Management, 2008, vol. 4, No. 2, pp. 383-394.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Ahren, Bo; "DPP-4 inhibitors", Best practice and research in clinical endocrinology and metabolism—New therapies for diabetes 200712 GB LNKD- DOI:10.1016/J. Beem.2007.07.005, vol. 21, No. 4, Dec. 2007, pp. 517-533.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.
American Diabetes Association, "Standards of Medical Care in Diabetes—2008." Diabetes Care, Jan. 2008, vol. 31, Supplement 1, pp. S12-S54.
Anstee, Quentin M. et al. "Mouse models in non-alcholic fatty liver disease and steatohepatitis research" (2006) International Journal of Expermental Pathology, vol. 87, pp. 1-16.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determination of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Aulinger, B.A. et al., "Ex-4 and the DPP-IV Inhibitor Vildagliptin have Additive Effects to Suppress Food Intake in Rodents". Abstract No. 1545-P, 2008.
Aulton, Michael E., Pharmaceutics: The Science of Dosage Form Design, Second Edition, 2002, pp. 441-448.
Baetta, R. et al., "Pharmacology of Dipeptidyl Peptidase-4 Inhibitors." Drugs, 2011, vol. 71, No. 11, pp. 1441-1467.
Balaban, Y.H.et al., "Dipeptidyl peptidase IV (DDP IV) in NASH patients" Annals of Hepatology, vol. 6, No. 4, Oct. 1, 2007, pp. 242-250, abstract.
Balbach, S. et al., "Pharmaceutical evaluation of early development candidates the 100 mg-approach." International Journal of Pharmaceutics, 2004, vol. 275, pp. 1-12.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.
Bastin, R.J. et al., "Salt Selection and Optimization Procedures for Pharmaceutical New Chemical Entities". Organic Process Research and Development, 2000, vol. 4, p. 427-435.
Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.
Berge, S. et al., "Pharmaceutical Salts." Journal of Pharmaceutical Sciences, 1977, vol. 66, No. 1, pp. 1-19.
Bernstein, Joel "Polymorphism in Molecular Crystals." Oxford University Press, 2002, p. 9.

(56) References Cited

OTHER PUBLICATIONS

Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.
Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Canadian Pharmacists Association, Compendium of Pharmaceuticals and Specialties, "Zestril" 2004, pp. 2289-2293.
Castello, R. et al., "Discoloration of Tablets Containing Amines and Lactose." Journal of Pharmaceutical Sciences, 1962, vol. 51, No. 2, pp. 106-108.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
ChemGaroo, "Leaving Group." 1999, Retrieved online: http://www.chemgapedia.de/vsengine/vlu/vsc/en/ch/12/oc/vluorganik/substitution/sn_2/sn 2. vlu/Page/vsc/en/ch/12/oc/substitution/sn_2/abgangsgrupen/abgangsgruppe. vscml.html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2-methyl-,S-(2-[[[1-(2-ethylbutyl)cyclohexyl}carbonyl}amino}pheyl}ester" . Formula: C23 H35 N O2 S. American Chemical Society. Sep. 20, 1998.

Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 N O3. American Chemical Society, Feb. 28, 2006.
Vincent, S.H. et al., "Metabolism and Excretion of the Dipeptidyl Peptidase 4 Inhibitor [14C]Sitagliptin in Humans." Drug Metabolism and Disposition, 2007, vol. 35, No. 4, pp. 533-538.
Yale, Jean-Francois, "Oral Antihyperglycemic Agents and Renal Disease: New Agents, New Concepts." Journal of the American Society of Nephrology, 2005, vol. 16, Suppl. 1, pp. S7-S10.
Yap, W.S. et al., "Review of management of type 2 diabetes mellitus." Journal of Clinical Pharmacy and Therapeutics, 1998, vol. 23, pp. 457-465.
Yokoyama< "Prevalence of albumineria and renal insufficiency and associated clinical factors in type 2 diabetes: the Japan Diabetes clinical data Management study(JDDM15)" Nephrol Dial Transplant (2009) 24: 1212-1219 Advance Access Pub 2008.
Zander, M. et al., "Additive Glucose-Lowering Effects of Glucagon-Like Peptide-1 and Metformin in Type 2 Diabetes." Diabetes Care, 2001, vol. 24, No. 4, pp. 720-725.
Zerilli, T. et al., "Sitagliptin Phosphate: A DPP-4 Inhibitor for the Treatment of Type 2 Diabetes Mellitus." Clinical Therapeutics, 2007, vol. 29, No. 12, pp. 2614-2634.
Banker, Gilbert S., "Prodrugs." Modern Pharmaceutics Third Edition, Marcel Dekker, Inc., 1996, p. 596, 3 pages.
Cao, C. et al., "The clinical application of linagliptin in Asians." Therapeutics and Clinical Risk Management, 2015, vol. 11, pp. 1409-1419.
Chowhan, Z.T. et al., Drug-Excipient Interaction Resulting from Powder Mixing IV: Role of Lubricants and Their Effect on In Vitro Dissolution, Journal of Pharmaceutical Sciences, 1986, vol. 75, No. 6, pp. 542-545.
Januvia, 25mg, 50mg, 100 mg, Summary of Product Characteristics, 2015, www.medicines.org.uk/EMC <http://www.medicines.org.uk/EMC>, pp. 1-32.
Kuno, Y. et al., "Effect of the type of lubricant on the characteristics of orally disintegrating tablets manufactured using the phase transition of sugar alcohol." European Journal of Pharmaceutics and Biopharmaceutics, 2008, vol. 69, pp. 986-992.
Nar, Herbert "Analysis of Binding Kinetics and Thermodynamics of DPP-4 Inhibitors and their Relationship to Structure." 2nd NovAliX Conference: Biophysics in drug discovery, Strasbourg, France, Jun. 9-12, 2015.
Schnapp, G. et al., "Analysis of Binding Kinetics and Thermodynamics of DPP-4 Inhibitors and their Relationship to Structure." 23rd PSDI, Protein Structure Determination in Industry, Tegernsee, Germany, Nov. 8-10, 2015.
Schnapp, G. et al., "Analysis of binding kinetics and thermodynamics of DPPIV Inhibitors and their relationship to structure." International Workshop: The aspect of time in drug design, Schloss Rauischholzhausen, Marburg, Germany, Mar. 24-27, 2014, 2 pages.
Schnapp, G. et al., "Comparative Enzyme Kinetic Analysis of the Launched DPP-4 Inhibitors." American Diabetes Association 74th Scientific Sessions, Poster 1048-P, 2014, 2 pages.
Schnapp, G. et al., "Comparative Enzyme Kinetic Analysis of the Launched DPP-4 Inhibitors." American Diabetes Association, Abstract 1048-P, 2014.
Wikipedia, "Linagliptin" Sep. 12, 2015. <https://en.wikipedia.org/w/index.php?title=Linagliptin&oldid=333469979>.
Zeeuw, D. et al., "Albuminuria, a Therapeutic Target for Cardiovascular Protection in Type 2 Diabetic Patients With Nephropathy." Circulation, 2004, vol. 110, No. 8, pp. 921-927.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Hocher, B. et al., "The novel DPP-4 inhibitors linagliptin and BI 14361 reduce infarct size after myocardial ischemia/reperfusion in rats." International Journal of Cardiology, 2013, vol. 167, pp. 87-93.
Holman, et al., "Addition of biphasic, prandial, or basal insulin to oral therapy in type 2 diabetes", N. England Journal Medicine, p. 1716-1730, 2007.

(56) References Cited

OTHER PUBLICATIONS

Horsford, E. N. "On the source of free hydrochloric acid in the gastric juice." Proceedings of the Royal Society of London, Published in 1868-1869, vol. 17, pp. 391-395.

Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

Hull, R. et al., "Nephrotic syndrome in adults." British Medical Journal, 2008, vol. 336, pp. 1185-1190.

Hunziker, D. et al, "Inhibitors of DPP IV—recent advances and structural views", Current Topics in Medicinal Chemistry, 2005, vol. 5 issue 16, pp. 1623-1637.

Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.

International Search Report and Written Opinion for PCT/EP2011/057256 dated Jul. 22, 2011.

Inukai, T., "Treatment of Diabetes in Patients for Whom Metformin Treatment is Not Appropriate." Modern Physician, 2008, vol. 28, No. 2, pp. 163-165.

Isomaa, B. et al., "Cardiovascular Morbidity and Mortality Associated With the Metabolic Syndrome." Diabetes Care, 2001, vol. 24, No. 4, pp. 683-689.

Iwamoto, Yasuhiko, "Insulin Glargine." Nippon Rinsho, 2002, vol. 60, Suppl. 9, pp. 503-515.

Januvia; Patient Information; 2010.

Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 3, pp. 1-10.

Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.

John Hopkins Children's Center, "Liver Disorders and Diseases." Retrieved online May 26, 2014 <http://www.hopkinschildrens.org/non-alcoholic-fatty-liver-disease.aspx>.

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

Kanada, S. et al., "Safety, tolerability, pharmacokenetics and pharmacodynamics of multiple doses of BI 1356.(proposed tradename Ondero), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.

Kelly. T., "Fibroblast activation protein-cx and dipeptidyl peptidase IV (CD26)P: Cell-surface proteases that activate cell signaling and are potential targets for cancern therapy". Drug Resistence Update 8, 2005, vol. 8. No. 1-2, pp. 51-58.

Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.

Kharkevich, D. A., "Educational Literature" Pharmacology (1987) Third Edition, Meditsina Press, Moscow pp. 47-48.

Kibbe, A., Editor. Handbook of Pharmaceutical Excipients, Third Edition, Copovidon—pp. 196-197, Date of Revision: Dec. 16, 2008. Mannitol—pp. 424-425, Date of Revision: Feb. 19, 2009, Published in 2009.

Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.

Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Kim, Kwang-Rok et al., "KR-62436, 6-{2-{2-(5-cyano4,5-dihydropyrazol-1-yl)-2-oxoethylamino}ethylamino} nicotinonitrile, is a novel dipeptidyl peptidase-IV (DDP-IV inhibitor with anti-hyperglycemic activity" European Journal of Pharmacology 518, 2005, p. 63-70.

Klein, T. et al., "Linagliptin alleviates hepatic steatosis and inflammation in a mouse model of non-alcoholic steatohepatitis." Medical Molecular Morphology, 2014, vol. 47, pp. 137-149.

Knorr, M. et al., "Comparison of Direct and Indirect Antioxidant Effects of Linagliptin (BI 1356, Ondero) with other Gliptins— Evidence for Anti-Inflammatory Properties of Linagliptin". Free Radical Biology and medicine, Elsevier Science, U.S. vol. 49, Oct. 23, 2010, p. S197.

Komori, Kiyoshi., "Treatment of Diabetes in Patients for Whom Metforming Treatment is Not Appropriate" Modern Physician (2008) vol. 28, No. 2 pp. 163-165.

Konstantinou, D. M. et al., "Pathophysiology-based novel pharmacotherapy for heart failure with preserved ejection fraction." Pharmacology & Therapeutics, 2013, vol. 140, No. 2, pp. 156-166.

Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.

Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.

Kumar, V. et al., "Maillard Reaction and Drug Stability." Maillard Reactions in Chemistry, Food, and Health, 1994, No. 151, pp. 20-27.

Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.

Lakatos, P. L. et al., "Elevated serum dipeptidyl peptidase IV (CD26, EC 3.4.14.5) activity in patients with primary biliary cirrhosis." Journal of Hepatol, 1999, vol. 30, p. 740.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

Lee Jones, K. et al., "Effect of Metformin in Pediatric Patients With Type 2 Diabetes." Diabetes Care, 2002, vol. 25, No. 1, pp. 89-94.

Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.

Levien,T.L. et al, "New drugs in development for the treatment of diabetes", Diabetes Spectrum, American Diabetes Association, US, vol. 22, No. 2, Jan. 1, 2009, pp. 92-106.

Lieberman, H. et al., "Pharmaceutical Dosage Forms." Marcel Dekker, Inc., 1980, vol. 1, p. 38.

(56) References Cited

OTHER PUBLICATIONS

Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.

Linagliptin Monograph, Published by VACO PBM-SHG US Veteran's Administration, 2011, pp. 1-17.

Lovshin, J.A. et al., "Incretin-based therapies for type 2 diabetes mellitus." Nature Reviews Endocrinology, 2009, vol. 5, pp. 262-269.

Lyssenko, V. et al., "Mechanisms by which common variants in the TCF7L2 gene increase risk of type 2 diabetes." The Journal of Clinical Investigation, 2007, vol. 117, No. 8, pp. 2155-2163.

March, J. "Advanced Organic Chemistry: Reactions, Mechanisms, and Structure". Fourth Edition, 1992, pp. 652-653.

Matsumiya, Teruhiko, et al., "Therapeutic Drugs for Clinicians" Diagnosis and Treatment (2008) vol. 96, No. 2 pp. 389-390.

Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.

McNay, David E.G. et al., "High fat diet causes rebound weight gain." Molecular Metabolism, 2013, vol. 2, pp. 103-108.

Medline Plus, "Obesity" 2013, Retrieved from internet on Aug. 22, 2013, http://www.nlm.nih.gov/medlineplus/obesity.html.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Shu, L et al., "Transcription Factor 7-Like 2 Regulates B-Cell Survival and Function in Human Pancreatic Islets." Diabetes, 2008, vol. 57, pp. 645-653.

Silverman, G. et al., "Handbook of Grignard Reagents." 1996, Retrieved online: <http://books.google.com/books?id=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.

Singhal, D. et al., "Drug polymorphism and dosage form design: a practical perspective." Advanced Drug Delivery Reviews, 2004, vol. 56, pp. 335-347.

Sorting, M.A. et al., "Linagliptin: a thorough characterization beyond its clinical efficacy." Frontiers in Endocrinology, 2013, vol. 4, Article 16, pp. 1-9.

St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.

Stahl, P.H., "Handbook of Pharmaceutical Salts" C.G. Wermuth, Wiley-VCH, 2002, pp. 1-374.

Standl, E. et al., "Diabetes and the Heart." Diabetes Guidelines (DDG), 2002, pp. 1-25.

Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.

Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.

Tadayyon, M. et al., "Insulin sensitisation in the treatment of Type 2 diabetes." Expert Opinion Investigative Drugs, 2003, vol. 12, No. 3, pp. 307-324.

Takai, S. et al., "Significance of Vascular Dipeptidyl Peptidase-4 Inhibition on Vascular Protection in Zucker Diabetic Fatty Rats." Journal of Pharmacological Sciences, 2014, vol. 125, pp. 386-393.

Takeda Press Release: "Voglibose (BASEN) for the prevention of type 2 diabetes mellitus: A Randomized, Doubleblind Trial in Japanese Subjects with Impaired Glucose Tolerance." 2008, Retrieved online Jul. 6, 2015. https://www.takeda.com/news/2008/20080526_3621.html, 2 pages.

Tamm, E, et al., "Double-blind study comparing the immunogenicity of a licensed DTwPHib-CRM197 conjugate vaccine (Quattvaxem TM) with three investigational, liquid formulations using lower doses of HIB-CRM197 conjugate". Science Direct, Vaccine, Feb. 2005, vol. 23, No. 14, p. 1715-1719.

Tanaka, S.. et al: "Suppression of Arthritis by the Inhibitors of Dipeptidyl Peptidase IV," In. J. Immunopharmac., vol. 19, No. 1, pp. 15-24, 1997.

Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.

Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.

Third Party Observation for application No. EP20070728655, May 13, 2013.

Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors." Journal of Pharmacology and Experimental Therapeutics, 2008, vol. 325, No. 1, pp. 175-182.

Thornber, C.W., "Isosterism and Molecular Modification in Drug Design." Chemical Society Reviews, 1979, pp. 563-580.

Tounyoubyou, "Symposium-19: Future Perspectives on Incretion Therapy in Diabetes." 2008, vol. 51, Suppl. 1, p. S-71, S19-2.

Tradjenta, Highlights of Prescribing Information (revised Sep. 2012).

Tribulova, N. et al. "Chronic Disturbances in NO Production Results in Histochemical and Subcellular Alterations of the Rat Heart." Physiol. Res., 2000, vol. 49, No. 1, pp. 77-88.

Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.

Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013. <http://www.abstractsonline.com/Plan/ViewAbstract.aspx?sKey=e68ac573-fe45-4c2f-9485-6270854fc10b&cKey=3c387569-04de-4f8c-b025-b358df91ca64&mKey=%7b899l8D6D-3018-4EA9-9D4F-711F98A7AE5D%7d>.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Uhlig-Laske, B. et al., "Linagliptin, a Potent and Selective DPP-4 Inhibitior, is Safe and Efficacious in Patients with Inadequately

(56) References Cited

OTHER PUBLICATIONS

Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

United Healthcare, "Diabetes." Retrieved from internet on Aug. 22, 2013, http://www.uhc.com/source4women/health_topics/diabetesirelatedinformation/d0f0417b073bf11OVgnVCM1000002f1Ob10a_. htm.

Vichayanrat, A. et al., "Efficacy and safety of voglibose in comparison with acarbose in type 2 diabetic patients." Diabetes Research and Clinical Practice, 2002, vol. 55, pp. 99-103.

Vickers, 71st Scientific Session of the American Diabetes Association, "The DPP-4 inhibitor linagliptin is weight neutral in the DIO rat but inhibits the weight gain of DIO animals withdrawn from exenatide", vol. 60, Jul. 2011.

Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

Weber, Ann E., "Dipeptidyl Peptidase IV Inhibitors for the Treatment of Diabetes." Journal of Medicinal Chemistry, 2004, vol. 47, pp. 4135-4141.

WebMD, Autoimmune Diseases: What Are They? Who Gets Them? "What Are Autoimmune Disorders?" 2015, pp. 1-3. Retrieved online Jul. 9, 2015. http://www.webmd.com/a-to-z-guides/autoimmune-diseases.

Wertheimer, et al., "Drug Delivery Systems improve pharmaceutical profile and facilitate medication adherence", Adv. Therapy 22: p. 559-577 (2005).

White, John R. Jr., "Dipeptidyl Peptidase-IV Inhibitors: Phamacological Profile and Clinical Use". Clinical Diabetes, Apr. 2008, vol. 26, No. 2, pp. 53-57.

Wikipedia, Annulation. Jun. 23, 2008, http://en.wikipedia.org/wiki/Annelation.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

Wirth, D. et al., "Maillard Reaction of Lactose and Fluoxetine Hydrochloride, a Secondary Amine." Journal of Pharmaceutical Sciences, 1998, vol. 87, No. 1, pp. 31-39.

Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.

Wolff, M.E.: "Burger's Medicinal Chemistry and Drug Discovery" Fifth Edition, vol. 1: Principles and Practice, pp. 975-977, 1994, John Wiley & Sons, Inc.

World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.

X-Ray Diffraction. The United States Pharmacopeia, 2002, USP 25 NF20, p. 2088-2089.

Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.

Yasuda, et al. "E3024 3-but-2-ynyl-5-methyl-2-piperazin-1-yl-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.

Yoshikawa, Seiji et al.: Chemical Abstract of Japanese Patent No. WO 2003/104229 Preparation of purinone derivatives as dipeptidylpeptidase IV (DPP-IV) inhibitors, 2003.

Yoshioka, S. et al., "Stability of Drugs and Dosage Forms." Kluwer Academic Publishers, 2002, pp. 30-33, 14 pages.

Abstract for AU 2003280680, Jun. 18, 2004.

Abstract for AU 2009224546, Sep. 17, 2009.

Abstract in English for DE19705233, Aug. 13, 1998.

Actos Prescribing Information, 1999, pp. 1-26.

Ahren, B. et al., "Twelve- and 52-Week Efficacy of the Dipeptidyl Peptidase IV Inhibitor LAF237 in Metformin-Treated Patients With Type 2 Diabetes." Diabetes Care, 2004, vol. 27, No. 12, pp. 2874-2880.

American Association of Clinical Endocrinologists, "Medical Guidelines for Clinical Practice for the Management of Diabetes Mellitus." Endocrine Practice, 2007, col. 13, Suppl. 1, pp. 1-68.

Beauglehole, Anthony R., "N3-Substituted Xanthines as Irreversible Adenosine Receptor Antagonists." Ph.D. Thesis, Deakin University, Australia, 2000, pp. 1-168.

Canadian Diabetes Association, "Pharmacologic Management of Type 2 Diabetes." Canadian Journal of Diabetes, 2003, vol. 27, Suppl. 2, pp. S37-S42.

Chiasson, J.-L. et al., "The Synergistic Effect of Miglitol Plus Metformin Combination Therapy in the Treatment of Type 2 Diabetes." Diabetes Care, 2001, vol. 24, No. 6, pp. 989-994.

Clinical Trial Protocol, "A Randomised, Double-blind, Placebo-controlled, Five Parallel Groups Study Investigating the Efficacy and Safety of BI 1356 BS." Boehringer Ingelheim Pharmaceuticals, last updated on Jun. 24, 2014.

Clinical Trial, NCT00622284, clinicaltrials.gov, updated Feb. 22, 2008, 3 pages.

Clinical Trials NCT00601250, clinicaltrials.gov, Jan. 25, 2008, 3 pages.

Clinical Trials: NCT00103857, "A Multicenter, Randomized, Double-Blind Factorial Study of the Co-Administration of MK0431 and Metformin in Patients With Type 2 Diabetes Mellitus Who Have Inadequate Glycemic Control" last updated on Apr. 27, 2015, 4 pages.

Clinical Trials: NCT00309608, "Efficacy and Safety of BI 1356 BS (Linagliptin) in Combination With Metformin in Patients With type2 Diabetes" Boehringer Ingelheim Pharmaceuticals, last updated on Jun. 24, 2014, 3 pages.

Colorcon, "Lactose Replacement with Starch 1500 in a Direct Compression Formula." 2005, pp. 1-4.

Colorcon, "Reducing Coated Tablet Defects from Laboratory through Production Scale: Performance of Hypromellose or Polyvinyl Alcohol-Based Aqueous Film Coating Systems." Opadry II, 2009, pp. 1-7.

Deacon, Carolyn F., "Dipeptidyl peptidase 4 inhibition with sitagliptin: a new therapy for Type 2 diabetes." Expert Opinion on Investigational Drugs, 2007, vol. 16, No. 4, pp. 533-545.

Dittberner, S. et al., "Determination of the absolute bioavailability of BI 1356, a substance with non-linear pharmacokinetics, using a population pharmacokinetic modeling approach." Abstracts of the Annual Meeting of the Population Approach Group in Europe, 2007.

Dugi, K. et al., "Safety, tolerability, pharmacokinetics, and pharmacodynamics of BI 1356, a novel DPP-IV inhibitor with a wide therapeutic window." Diabetic Medicine, 2006, vol. 23, Suppl. 4, p. 300.

EMEA: European Medicines Agency, "Galvus (vildagliptin)" Retrieved online on Jan. 21, 2016, 6 pages.

Feng, J. et al., "Discovery of Alogliptin: A Potent, Selective, Bioavailable, and Efficacious Inhibitor of Dipeptidyl Peptidase IV." Journal of Medicinal Chemistry, 2007, vol. 50, No. 10, pp. 2297-2300.

Flatt, P.R. et al., "Dipeptidyl peptidase IV (DPP IV) and related molecules in type 2 diabetes." Frontiers in Bioscience, 2008, vol. 13, pp. 3648-3660.

(56) References Cited

OTHER PUBLICATIONS

Gall, "Prevalence of micro-and macroalbuminuria, arterial hypertension, retinopathy and large vessel disease in European type 2 (non-insulin dependent) diabetic patients", Diabetologia (1991) 655-661.
Gallwitz, B., "Safety and efficacy of linagliptin in type 2 diabetes patients with common renal and cardiovascular risk factors." Therapeutic Advances in Endocrinology and Metabolism, 2013, vol. 4, No. 3, pp. 95-105.
Galvus (Vildagliptin) Scientific Discussion, EMEA, 2007, pp. 1-34.
Garber, A.J. et al., "Simultaneous glyburide/metformin therapy is superior to component monotherapy as an initial pharmacological treatment for type 2 diabetes." Diabetes, Obesity and Metabolism, 2002, vol. 4, pp. 201-208.
Glucophage® Prescribing Information, 2001, 7 pages.
Goodarzi, M.O. et al., "Metformin revisited: re-evaluation of its properties and role in the pharmacopoeia of modem antidiabetic agents." Diabetes, Obesity and Metabolism, 2005, vol. 7, pp. 654-665.
Gwaltney, S.L. II et al., "Inhibitors of Dipeptidyl Peptidase 4." Annual Reports in Medicinal Chemistry, 2005, vol. 40, pp. 149-165.
Halimi, "Combination treatment in the management of type 2 diabetes: focus on vildagliptin and metformin as a single tablet", Vascular Health and Risk Management, 2008 481-92.
He, Y.L. et al., "The Influence of Renal Impairment on the Pharmacokinetics of Vildagliptin." Clinical Pharmacology & Therapeutics, 2007, vol. 81, Suppl. 1, Abstract No. PIII-86.
Hinke, S.A. et al., "Metformin Effects on Dipeptidylpeptidase IV Degradation of Glucagon-like Peptide-1." Biochemical and Biophysical Research Communications, 2002, vol. 291, No. 5, pp. 1302-1308.
Hinke, S.A. et al., "On Combination Therapy of Diabetes With Metformin and Dipeptidyl Peptidase IV Inhibitors." Diabetes Care, 2002, vol. 25, No. 8, pp. 1490-1492.
Hinnen, D. et al., "Incretin Mimetics and DPP-IV Inhibitors: New Paradigms for the Treatment of Type 2 Diabetes." Journal of The American Board of Family Medicine, 2006, vol. 19, No. 6, pp. 612-620.
Inzucchi, Silvio E., "Oral Antihyperglycemic Therapy for Type 2 Diabetes." The Journal of the American Medical Association, 2002, vol. 287, No. 3, pp. 360-372.
Janumet Prescribing Information, revised Jan. 2008, 22 pages.
Januvia Prescribing Information and Product Label, 2006, 36 pages.
Kiraly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.
Kirpichnikov, D. et al., "Metformin: An Update." Annals of Internal Medicine, 2002, vol. 137, No. 1, pp. 25-33.
Knowler, W.C. et al., "Reduction in the Incidence of Type 2 Diabetes with Lifestyle Intervention or Metformin." The New England Journal of Medicine, 2002, vol. 346, No. 6, pp. 393-403.
Lachman, L. et al., "The Theory and Practice of Industrial Pharmacy." Varghese Publishing House, Third Edition, 1987, pp. 190-194.
Lindsay, J.R. et al., "Inhibition of dipeptidyl peptidase IV activity by oral metformin in Type 2 diabetes." Diabetic Medicine, 2005, vol. 22, pp. 654-657.
Lu, "High prevlaence of albuminuria in population based patients diagnosed with type 2 diabetes in the Shanghai downtown", Diabestes Research and Clinical Practice (2007) 184-192.
Mathieu, C. et al., "Antihyperglycaemic therapy in elderly patients with type 2 diabetes: potential tole of incretin mimetics and DPP-4 inhibitors." International Journal of Clinical Practice, 2007, vol. 61, Suppl. 154, pp. 29-37.
Mikhail, Nasser, "Incretin mimetics and dipeptidyl peptidase 4 inhibitors in clinical trials for the treatment of type 2 diabetes." Expert Opinion on Investigational Drugs, 2008, vol. 17, No. 6, pp. 845-853.
Novartis AG, Investor Relations Release, "Galvus, a new oral treatment for type 2 diabetes, receives positive opinion recommending European Union approval." Securities and Exchange Commission, Form 6-K, 2007, pp. 1-4.
Pietruck, F. et al., "Rosiglitazone is a safe and effective treatment option of new-onset diabetes mellitus after renal transplantation." Transplant International, 2005, vol. 18, pp. 483-486.
Sulkin, T.V. et al., "Contraindications to Metformin Therapy in Patients With NIDDM." Diabetes Care, 1997, vol. 20, No. 6, pp. 925-928.
Turner, R.C. et al., "Glycemic Control With Diet, Sulfonylurea, Metformin, or Insulin in Patients With Type 2 Diabetes Mellitus Progressive Requirement for Multiple Therapies (UKPDS 49)" The Journal of the American Medical Association, 1999, vol. 281, No. 21, pp. 2005-2012.
Van Heek, M. et al., "Ezetimibe, a Potent Cholesterol Absorption Inhibitor, Normalizes Combined Dyslipidemia in obese Hyperinsulinemic Hamsters." Diabetes, 2001, vol. 50, pp. 1330-1335.
Mendes, F.D, et al. "Recent advances in the treatment of non-alcoholic fatty liver disease". Expert Opinion on Investigational Drugs, vol. 14, No. 1, Jan. 1, 2005, p. 29-35.
Merck Manual of Diagnosis and Therapy: "Obesity." 1999, 17th Edition, Chapter 5, pp. 58-62.
Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.
MIMS Jan. 2009, "Sitagliptin." pp. 152-153, 3 pages.
Nabors, Lyn O'Brien "Alternative Sweeteners." Marcel Dekker, Inc., 2001, pp. 235, 339-340.
Naik, R. et al., "Latent Autoimmune Diabetes in Adults." The Journal of Clinical Endocrinology and Metabolism, 2009, vol. 94, No. 12, pp. 4635-4644.
Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.
National Program for Care Guidelines, "Type 2 Diabetes mellitus." 2002, First Edition, pp. 1-50.
Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.
Nielsen, L., "Incretin Mimetics and DPP-IV Inhibitors for the Treatment of Type 2 Diabetes." DDT, 2005, vol. 10, No. 10, pp. 703-710.
Nihon Ijinpo, Japan Medicinal Journal, 2001, No. 4032, p. 137.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Office Action for U.S. Appl. No. 10/695,597 mailed May 2, 2008.
Oz, Helieh S., "Methionine Deficiency and Hepatic Injury in a Dietary Steatohepatitis Model." Digestive Diseases and Sciences, 2008, vol. 53, No. 3, pp. 767-776.
Patani George A. et al.: "Bioisoterism : A Rational Approach in Drug Design", Chemical Reviews, 1996, vol. 96, No. 8, pp. 3147-3176.
Pearson, E. R. et al., "Variation in TCF7L2 Influences Therapeutic Response to Sulfonylureas." Diabetes, 2007, vol. 56, pp. 2178-2182.
Pei, Z.: "From the bench to the bedside: Dipeptidyl peptidase IV inhibitors, a new class of oral antihyperglycemic agents" Current

(56) References Cited

OTHER PUBLICATIONS

Opinion in Drug Discovery and Development, Current Drugs, London, GB vol. 11, No. 4, Jul. 1, 2008 pp. 512-532.
Plummer, C.J.G. et al., "The Effect of Melting Point Distributions on DSC Melting Peaks." Polymer Bulletin, 1996, vol. 36, pp. 355-360.
Pospisilik, et al; Dipeptidyl Peptidase IV Inhibitor Treatment Stimulates ?-Cell Survival and Islet Neogenesis in Streptozotocin-Induced Diabetic Rats; Diabetes, vol. 52, Mar. 2003 pp. 741-750.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Pratley, R. et al., "Inhibition of DPP-4: a new therapeutic approach for the treatment of type 2 diabetes." Current Medical Research and Opinion, 2007, vol. 23, No. 4, pp. 919-931.
Prescribing Information, Package insert for Leprinton tablets 100mg, Manufacturer: Tatsumi Kagaku Co., Ltd., Mar. 2003, pp. 1-3.
Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.
Radermecker, Regis et al., "Lipodystrophy Reactions to Insulin." American Journal of Clinical Dermatology, 2007, vol. 8, pp. 21-28.
Rask-Madsen, C. et al., "Podocytes lose their footing." Nature, 2010, vol. 468, pp. 42-44.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Rosenbloom, et al., "Type 2 Diabetes mellitus in the child and adolescent", Pediatric Diabetes, 2008, p. 512-526.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Rowe, R. et al., Handbook of Pharmaceutical Excipients, Fifth Edition, Pharmaceutical Press, 2006, pp. 389-395, 449-453, and 731-733.
Rowe, R. et al., Handbook of Pharmaceutical Excipients, Fourth Edition, Pharmaceutical Press and American Pharmaceutical Association, 2003, pp. 323-332.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sarafidis, P. et al., "Cardiometabolic Syndrome and Chronic Kidney Disease: What is the link?" JCMS 2006, 1: p. 58-65.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Schillinger, M. et al., "Restenosis after percutaneous angioplasty: the role of vascular inflammation." Vascular Health and Risk Management, 2005, vol. 1, No. 1, pp. 73-78.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.
Schwartz, M. S. et al., "Type 2 Diabetes Mellitus in Childhood: Obesity and Insulin Resistance". JAOA Review Article, vol. 108, No. 9, Sep. 2008, p. 518.
Scientific Discussion, EMEA, Pramipexole, 2005, pp. 1-10.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Shanks, N. et al., Are animal models predictive for humans?, PEHM, Philosophy, Ethics, and Humanaities in Medicine, 4(2), 2009, 1-20.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012. <http://www.abstractsonline.com/Plan/ViewAbstract.aspx?sKey=0b0017b9-9e90-4695-b9af-b6870e96a921&cKey=8eff47ae-db49-4036-a142-848ac068c405&mKey=2dbfcaf7-1539-42d5-8dda-0a94abb089e8>.
Sheperd, Todd M. et al., "Efective management of obesity." The Journal of Family Practice, 2003, vol. 52, No. 1, pp. 34-42.
Shintani, Maki, et al., "Insulin Resistance and Genes" Circulatory Sciences (1997) vol. 17, No. 12 pp. 1186-1188.
Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.
EMEA Guidelines on Eucreas®, 2007, pp. 1-27.
EMEA Guidelines on Galvus®, 2007, pp. 1-34.
Kishore, Preeti MD., "Complications of Diabetes Mellitus." Merck Manual Consumer Version, 2016, pp. 1-7.
Moritoh, Y. et al., "Combination treatment with alogliptin and voglibose increases active GLP-1 circulation, prevents the development of diabetes and preserves pancreatic beta-cells in prediabetic db/db mice." Diabetes, Obesity and Metabolism, 2010, vol. 12, pp. 224-233.
Rosenstock, J. et al., "Triple Therapy in Type 2 Diabetes." Diabetes Care, 2006, vol. 29, No. 3, pp. 554-559.
U.S. Appl. No. 15/235,575, filed Aug. 12, 2016, Inventor: Klaus Dugi.
Yasuda, N. et al., "Metformin Causes Reduction of Food Intake and Body Weight Gain and Improvement of Glucose Intolerance in Combination with Dipeptidyl Peptidase IV Inhibitor in Zucker fa/fa Rats." The Journal of Pharmacology and Experimental Therapeutics, 2004, vol. 310, No. 2, pp. 614-619.

SEQUENCE LISTING

<160> NUMBER OF SEQ ID NOS: 1

<210> SEQ ID NO 1
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: C-term NH2

<400> SEQUENCE: 1

```
His Val Glu Gly Thr Phe Thr Ser Asp Val Ser Ser Tyr Leu Glu Glu
1               5                   10                  15
Gln Ala Ala Lys Glu Phe Ile Ala Trp Leu Ile Lys Gly Gly Pro Ser
            20                  25                  30
Ser Gly Ala Pro Pro Pro Cys Cys
        35                  40
```

COMBINATION THERAPY

FIELD OF THE INVENTION

The present invention relates to methods for treating and/or preventing metabolic diseases, especially type 2 diabetes mellitus, obesity and/or conditions related thereto (e.g. diabetic complications) comprising the combined administration of a GLP-1 receptor agonist (e.g. exogenous GLP-1 or a GLP-1 analogue) and a certain DPP-4 inhibitor, to pharmaceutical compositions and combinations comprising such active components, and to certain therapeutic uses thereof.

BACKGROUND OF THE INVENTION

Type 2 diabetes mellitus is a common chronic and progressive disease arising from a complex pathophysiology involving the dual endocrine effects of insulin resistance and impaired insulin secretion with the consequence not meeting the required demands to maintain plasma glucose levels in the normal range. This leads to chronic hyperglycaemia and its associated micro- and macrovascular complications or chronic damages, such as e.g. diabetic nephropathy, retinopathy or neuropathy, or macrovascular (e.g. cardio- or cerebrovascular) complications. The vascular disease component plays a significant role, but is not the only factor in the spectrum of diabetes associated disorders. The high frequency of complications leads to a significant reduction of life expectancy. Diabetes is currently the most frequent cause of adult-onset loss of vision, renal failure, and amputation in the Industrialised World because of diabetes induced complications and is associated with a two to five fold increase in cardiovascular disease risk.

Furthermore, diabetes (particularly type 2 diabetes) is often coexistent and interrelated with obesity and these two conditions together impose a particularly complex therapeutic challenge. Because of the effects of obesity on insulin resistance, weight loss and its maintenance is an important therapeutic objective in overweight or obese individuals with prediabetes, metabolic syndrome or diabetes. Studies have been demonstrated that weight reduction in subjects with type 2 diabetes is associated with descreased insulin resistance, improved measures of glycemia and lipemia, and reduced blood pressure. Maintainance of weight reduction over longer term is considered to improve glycemic control and prevent diabetic complications (e.g. reduction of risk for cardiovascular diseases or events). Thus, weight loss is recommended for all overweight or obese individuals who have or are at risk for diabetes. However, obese patients with type 2 diabetes have much greater difficulty losing weight and maintain the reduced weight than the general non-diabetic population.

SUMMARY OF THE INVENTION

The present invention relates to a method for reducing and maintaining body weight and/or body fat in a patient in need thereof, such as e.g. in an overweight or obesity patient with or without diabetes (particularly type 2 diabetes patient being obese or overweight), comprising the combined (e.g. separate, simultaneous or sequential) administration of a GLP-1 receptor agonist (e.g. GLP-1 or GLP-1 analogue) and a certain DPP-4 inhibitor; preferably said method comprising the sequential administration of a GLP-1 receptor agonist followed by a certain DPP-4 inhibitor.

Furthermore, the present invention relates to a method for reducing and maintaining body weight and/or body fat in a patient in need thereof, such as e.g. in an overweight or obesity patient with or without diabetes (particularly type 2 diabetes patient being obese or overweight), comprising i) inducing body weight loss (e.g. by administering an effective amount of a GLP-1 receptor agonist to the patient) and ii.) administering an effective amount of a certain DPP-4 inhibitor to the patient.

Moreover, the present invention relates to a certain DPP-4 inhibitor for use in preventing of body weight and/or body fat gain or controlling, stabilizing or maintaining a reduced body weight and/or body fat followed discontinuation of weight reducing treatment (such as e.g. diet, exercise and/or treatment with an anti-obesity or body weight reducing agent), particularly after discontinuation of treatment with a GLP-1 receptor agonist.

Further, the present invention relates to a certain DPP-4 inhibitor for use in delaying body weight and/or body fat gain and/or maintaining reduction in body weight and/or body fat in a subject (particularly an obesity patient with or without diabetes), particularly subsequent to cessation of or withdrawn from body weight reducing and/or fat reducing treatment. Further, the present invention relates to a certain DPP-4 inhibitor for use in a method of delaying body weight and/or body fat gain and/or maintaining body weight and/or body fat loss induced by treatment with a GLP-1 receptor agonist in a subject, said method comprising cessation of GLP-1 receptor agonist treatment and transferring the subject from GLP-1 receptor agonist to DPP-4 inhibitor treatment.

Furthermore, the present invention relates to a DPP-4 inhibitor for use in reducing, maintaining loss of or delaying increase of body weight and/or body fat in a subject actively putting on weight.

Yet furthermore, the present invention relates to a DPP-4 inhibitor for use in reducing, maintaining loss of or delaying increase of body weight and/or body fat in a subject being in condition of actively putting on weight and/or increasing body weight through the deposition of fat, such as e.g. after withdrawing a weight loss treatment or under a treatment associated with weight gain (e.g. through the action of sulphonylureas, glinides, insulin and/or thiazolidinediones, the use of which is associated with weight gain).

Further, the present invention relates to a certain DPP-4 inhibitor for use in reducing intra-myocellular fat and/or hepatic fat in a patient in need thereof, such as e.g. in an overweight or obesity patient with or without diabetes (particularly type 2 diabetes patient being obese or overweight).

Further, the present invention relates to a DPP-4 inhibitor for use in achieving a reduction in the dose of GLP-1 receptor agonist medication, e.g. required for effective therapy of metabolic diseases (such as e.g. type 2 diabetes mellitus, obesity and/or conditions related thereto (e.g. diabetic complications)), e.g. in an overweight or obesity patient with or without diabetes (particularly type 2 diabetes patient being obese or overweight).

Moreover, the present invention relates to a certain DPP-4 inhibitor for use in treating, preventing or reducing the risk of skin necrosis, particularly associated with or induced by infusions or injections, e.g. of a GLP-1 receptor agonist, insulin or insulin analogue or other drugs administered subcutaneously and/or via needle or syringe, typically pierced through the skin.

Further, the present invention relates to the DPP-4 inhibitors and/or GLP-1 receptor agonists, each as defined herein, for use in the combination therapies as described herein.

DETAILED DESCRIPTION OF THE INVENTION

Figure 1:
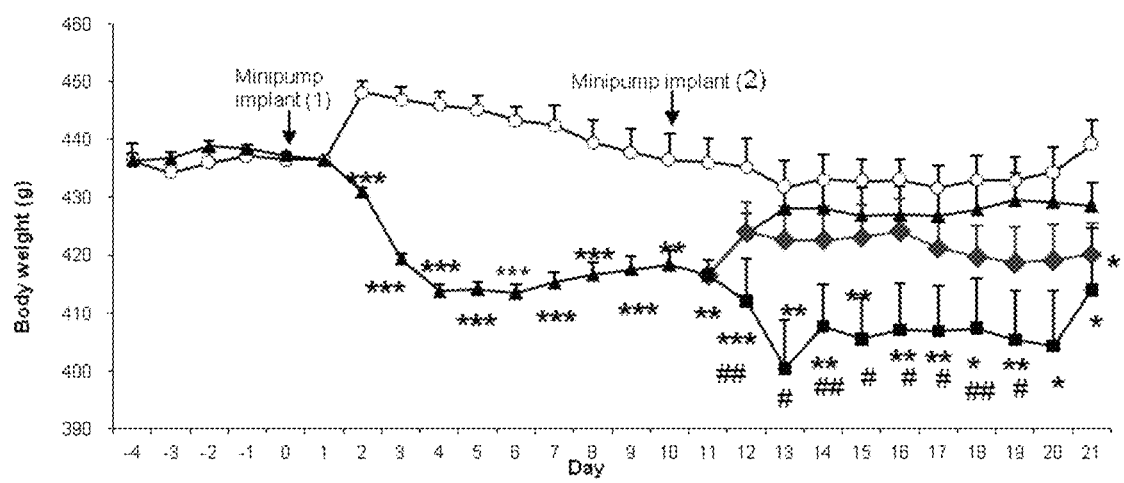
FIG. 1 shows body weight development in animals treated with Vehicle (-○-) (n=7); Exatinide 30 μg/kg/day (Day 1-10)+Vehicle (from Day 11) (-▲-) (n=9); Exatinide 30 μg/kg/day (Day 1-10)+BI 1356 3 mg/kg po (from Day 11) (-♦-) (n=8); and Exatinide 30 μg/kg/day (-■-) (n=5). Results are adjusted means+sem; n=5-51 (n values in brackets are the number remaining on day 21.). SEMs are calculated from the residuals of the statistical model. Data analysed by ANCOVA with body weight on Day 1 as covariate. Multiple comparisons versus the vehicle control group are by multiple t test. Significant differences from vehicle control: *$p<0.05$, $p<0.01$, *$p<0.001$. Significant differences from Exenatide 30 μg/kg/day (Day 1-10)+vehicle (from Day 11): #$p<0.05$, ##$p<0.01$ (multiple t test). Percent values are weight loss compared to Vehicle on Day 21.

Overweight may be defined as the condition wherein the individual has a body mass index (BMI) greater than or 25 kg/m² and less than 30 kg/m². The terms "overweight" and "pre-obese" are used interchangeably.

Obesity may be defined as the condition wherein the individual has a BMI equal to or greater than 30 kg/m². According to a WHO definition the term obesity may be categorized as follows: class I obesity is the condition wherein the BMI is equal to or greater than 30 kg/m² but lower than 35 kg/m²; class II obesity is the condition wherein the BMI is equal to or greater than 35 kg/m² but lower than 40 kg/m²; class III obesity is the condition wherein the BMI is equal to or greater than 40 kg/m².

Obesity may include e.g. visceral or abdominal obesity.

Visceral obesity may be defined as the condition wherein a waist-to-hip ratio of greater than or equal to 1.0 in men and 0.8 in women is measured. It defines the risk for insulin resistance and the development of pre-diabetes.

Abdominal obesity may usually be defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

Diabetes patients within the meaning of this invention may include patients having obesity or overweight.

Obesity patients within the meaning of this invention may include, in one embodiment, patients with diabetes (particularly having type 2 diabetes).

Obesity patients within the meaning of this invention may include, in another embodiment, patients without diabetes (particularly without type 1 or type 2 diabetes).

The treatment of type 2 diabetes typically begins with diet and exercise, followed by oral antidiabetic monotherapy, and although conventional monotherapy may initially control blood glucose in some patients, it is however associated with a high secondary failure rate. The limitations of single-agent therapy for maintaining glycemic control may be overcome, at least in some patients, and for a limited period of time by combining multiple drugs to achieve reductions in blood glucose that cannot be sustained during long-term therapy with single agents. Available data support the conclusion that in most patients with type 2 diabetes current monotherapy will fail and treatment with multiple drugs will be required.

But, because type 2 diabetes is a progressive disease, even patients with good initial responses to conventional combination therapy will eventually require an increase of the dosage or further treatment with insulin because the blood glucose level is very difficult to maintain stable for a long period of time. Although existing combination therapy has the potential to enhance glycemic control, it is not without limitations (especially with regard to long term efficacy). Further, traditional therapies may show an increased risk for side effects, such as hypoglycemia or weight gain, which may compromise their efficacy and acceptability.

Thus, for many patients, these existing drug therapies result in progressive deterioration in metabolic control despite treatment and do not sufficiently control metabolic status especially over long-term and thus fail to achieve and to maintain glycemic control in advanced or late stage type 2 diabetes, including diabetes with inadequate glycemic control despite conventional oral or non-oral antidiabetic medication.

Therefore, although intensive treatment of hyperglycemia can reduce the incidence of chronic damages, many patients with type 2 diabetes remain inadequately treated, partly because of limitations in long term efficacy, tolerability and dosing inconvenience of conventional antihyperglycemic therapies.

In addition, obesity, overweight or weight gain (e.g. as side or adverse effect of some conventional antidiabetic medications) further complicates the treatment of diabetes and its microvascular or macrovascular complications.

This high incidence of therapeutic failure is a major contributor to the high rate of long-term hyperglycemia-associated complications or chronic damages (including micro- and macrovascular complications such as e.g. diabetic nephropathy, retinopathy or neuropathy, or cardiovascular complications) in patients with type 2 diabetes.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides and α-glucosidase inhibitors.

Non-oral (typically injected) antidiabetic drugs conventionally used in therapy (such as e.g. first- or second-line, and/or mono- or (initial or add-on) combination therapy) include, without being restricted thereto, GLP-1 or GLP-1 analogues, and insulin or insulin analogues.

However, the use of these conventional antidiabetic or antihyperglycemic agents can be associated with various adverse effects. For example, metformin can be associated with lactic acidosis or gastrointestinal side effects; sulfonylureas, glinides and insulin or insulin analogues can be associated with hypoglycemia and weight gain; thiazolidinediones can be associated with edema, bone fracture, weight gain and heart failure/cardiac effects; and alpha-glucosidase blockers and GLP-1 or GLP-1 analogues can be associated with gastrointestinal adverse effects (e.g. dyspepsia, flatulence or diarrhea, or nausea or vomiting) and, most seriously (but rare), pancreatitis.

Therefore, it remains a need in the art to provide efficacious, safe and tolerable antidiabetic therapies, particularly for obese or overweight diabetes patients.

Further, it remains a need in the art to provide efficacious, safe and tolerable therapies for obesity patients with or without diabetes, particularly for reducing body weight and maintaining reduced body weight as well as for preventing rebound of weight gain following cessation of weight loss treatment in such patients.

Within the management of the dual epidemic of type 2 diabetes and obesity ("diabesity"), it is an objective to find therapies which are safe, tolerable and effective in the treatment or prevention of these conditions together, particularly in achieving long term weight reduction and improving glycemic control.

Further, within the therapy of type 2 diabetes, obesity or both, it is a need for treating the condition effectively, avoiding the complications inherent to the condition, and delaying disease progression.

Furthermore, it remains a need that antidiabetic treatments not only prevent the long-term complications often found in advanced stages of diabetes disease, but also are a therapeutic option in those diabetes patients who have developed complications, such as renal impairment.

Moreover, it remains a need to provide prevention or reduction of risk for adverse effects associated with conventional antidiabetic therapies.

The enzyme DPP-4 (dipeptidyl peptidase IV) also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

For example, DPP-4 inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769, WO2007/014886; WO 2004/050658, WO 2004/111051, WO 2005/058901, WO 2005/097798; WO 2006/068163, WO 2007/071738, WO 2008/017670; WO 2007/128721, WO 2007/128724, WO 2007/128761, or WO 2009/121945.

Glucagon-like peptide-1 (GLP-1) is a hormon secreted from enteroendocrine L cells of the intestine in response to food. Exogenous GLP-1 administration at pharmacological doses results in effects that are beneficial for treating type 2 diabetes. However, native GLP-1 is subject to rapid enzymatic degradation. The action of GLP-1 is mediated through the GLP-1 receptor (GLP-1R).

In the monitoring of the treatment of diabetes mellitus the HbA1c value, the product of a non-enzymatic glycation of the haemoglobin B chain, is of exceptional importance. As its formation depends essentially on the blood sugar level and the life time of the erythrocytes the HbA1c in the sense of a "blood sugar memory" reflects the average blood sugar level of the preceding 4-12 weeks. Diabetic patients whose HbA1c level has been well controlled over a long time by more intensive diabetes treatment (i.e. <6.5% of the total haemoglobin in the sample) are significantly better protected from diabetic microangiopathy. The available treatments for diabetes can give the diabetic an average improvement in their HbA1c level of the order of 1.0-1.5%. This reduction in the HbA1C level is not sufficient in all diabetics to bring them into the desired target range of <7.0%, preferably <6.5% and more preferably <6% HbA1c.

Within the meaning of this invention, inadequate or insufficient glycemic control means in particular a condition wherein patients show HbA1c values above 6.5%, in particular above 7.0%, even more preferably above 7.5%, especially above 8%. An embodiment of patients with inadequate or insufficient glycemic control include, without being limited to, patients having a HbA1c value from 7.5 to 10% (or, in another embodiment, from 7.5 to 11%). A special sub-embodiment of inadequately controlled patients refers to patients with poor glycemic control including, without being limited, patients having a HbA1c value ≥9%.

Within glycemic control, in addition to improvement of the HbA1c level, other recommended therapeutic goals for type 2 diabetes mellitus patients are improvement of fasting plasma glucose (FPG) and of postprandial plasma glucose (PPG) levels to normal or as near normal as possible. Recommended desired target ranges of preprandial (fasting) plasma glucose are 70-130 mg/dL (or 90-130 mg/dL) or <110 mg/dL, and of two-hour postprandial plasma glucose are <180 mg/dL or <140 mg/dL.

In one embodiment, diabetes patients within the meaning of this invention may include patients who have not previously been treated with an antidiabetic drug (drug-naïve patients). Thus, in an embodiment, the therapies described herein may be used in naïve patients. In another embodiment, diabetes patients within the meaning of this invention may include patients with advanced or late stage type 2 diabetes mellitus (including patients with failure to conventional antidiabetic therapy), such as e.g. patients with inadequate glycemic control on one, two or more conventional oral and/or non-oral antidiabetic drugs as defined herein, such as e.g. patients with insufficient glycemic control despite (mono-)therapy with metformin, a thiazolidinedione (particularly pioglitazone), a sulphonylurea, a glinide, GLP-1 or GLP-1 analogue, insulin or insulin analogue, or an α-glucosidase inhibitor, or despite dual combination therapy with metformin/sulphonylurea, metformin/thiazolidinedione (particularly pioglitazone), metformin/insulin, pioglitazone/sulphonylurea, pioglitazone/insulin, or sulphonylurea/insulin. Thus, in an embodiment, the therapies described herein may be used in patients experienced with therapy, e.g. with conventional oral and/or non-oral antidiabetic mono- or dual or triple combination medication as mentioned herein.

A further embodiment of diabetic patients within the meaning of this invention refers to patients ineligible for metformin therapy including
  patients for whom metformin therapy is contraindicated, e.g. patients having one or more contraindications against metformin therapy according to label, such as for example patients with at least one contraindication selected from:
    renal disease, renal impairment or renal dysfunction (e.g., as specified by product information of locally approved metformin), dehydration,
    unstable or acute congestive heart failure,
    acute or chronic metabolic acidosis, and
    hereditary galactose intolerance;
and
  patients who suffer from one or more intolerable side effects attributed to metformin, particularly gastrointestinal side effects associated with metformin, such as for example patients suffering from at least one gastrointestinal side effect selected from:
    nausea,
    vomiting,
    diarrhoea,
    intestinal gas, and
    severe abdominal discomfort.

A further embodiment of the diabetes patients which may be amenable to the therapies of this invention may include, without being limited, those diabetes patients for whom normal metformin therapy is not appropriate, such as e.g. those diabetes patients who need reduced dose metformin therapy due to reduced tolerability, intolerability or contraindication against metformin or due to (mildly) impaired/reduced renal function (including elderly patients, such as e.g. ≥60-65 years).

A further embodiment of diabetic patients within the meaning of this invention refers to patients having renal disease, renal dysfunction, or insufficiency or impairment of renal function (including mild, moderate and severe renal impairment), e.g. as suggested by elevated serum creatinine levels (e.g. serum creatinine levels above the upper limit of normal for their age, e.g. 130-150 µmol/l, or 1.5 mg/dl 136 µmol/l) in men and ≥1.4 mg/dl (≥124 µmol/l) in women) or abnormal creatinine clearance (e.g. glomerular filtration rate (GFR) ≤30-60 ml/min).

In this context, for more detailed example, mild renal impairment may be e.g. suggested by a creatinine clearance of 50-80 ml/min (approximately corresponding to serum creatine levels of ≤1.7 mg/dL in men and ≤1.5 mg/dL in women); moderate renal impairment may be e.g. suggested by a creatinine clearance of 30-50 ml/min (approximately corresponding to serum creatinine levels of >1.7 to ≤3.0 mg/dL in men and >1.5 to ≤2.5 mg/dL in women); and severe renal impairment may be e.g. suggested by a creatinine clearance of <30 ml/min (approximately corresponding to serum creatinine levels of >3.0 mg/dL in men and >2.5 mg/dL in women). Patients with end-stage renal disease require dialysis (e.g. hemodialysis or peritoneal dialysis).

For other more detailed example, patients with renal disease, renal dysfunction or renal impairment include patients with chronic renal insufficiency or impairment, which can be stratified according to glomerular filtration rate (GFR, ml/min/1.73 m$^2$) into 5 disease stages: stage 1 characterized by normal GFR≥90 plus either persistent albuminuria or known structural or hereditary renal disease; stage 2 characterized by mild reduction of GFR (GFR 60-89) describing mild renal impairment; stage 3 characterized by moderate reduction of GFR (GFR 30-59) describing moderate renal impairment; stage 4 characterized by severe reduction of GFR (GFR 15-30) describing severe renal impairment; and terminal stage 5 characterized by requiring dialysis or GFR<15 describing established kidney failure (end-stage renal disease, ESRD).

Within the scope of the present invention it has now been found that certain DPP-4 inhibitors as defined herein as well as pharmaceutical combinations, compositions or combined uses according to this invention of these DPP-4 inhibitors and GLP-1 receptor agonists (e.g. exogenous GLP-1 or GLP-1 analogues) as defined herein have unexpected and particularly advantageous properties, which make them suitable for the purpose of this invention and/or for fulfilling one or more of above needs.

The present invention thus relates to a combination comprising a certain DPP-4 inhibitor (particularly BI 1356) and a GLP-1 receptor agonist (e.g. exogenous GLP-1 or a GLP-1 analogue), each as defined herein, particularly for simultaneous, separate or sequential use in the therapies described herein.

The present invention further relates to a method for treating and/or preventing metabolic diseases, especially type 2 diabetes mellitus, obesity and/or conditions related thereto (e.g. diabetic complications) comprising the combined (e.g. simultaneous, separate or sequential) administration of an effective amount of a GLP-1 receptor agonist (e.g. exogenous GLP-1 or a GLP-1 analogue) as defined herein and of an effective amount of a DPP-4 inhibitor as defined herein to the patient (particularly human patient) in need thereof, such as e.g a patient as described herein.

The present invention further relates to at least one of the following methods:
  preventing, slowing the progression of, delaying or treating a metabolic disorder or disease, such as e.g. type 1 diabetes mellitus, type 2 diabetes mellitus, impaired glucose tolerance (IGT), impaired fasting blood glucose (IFG), hyperglycemia, postprandial hyperglycemia, overweight, obesity, dyslipidemia, hyperlipidemia, hypercholesterolemia, hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome;
  improving glycemic control and/or for reducing of fasting plasma glucose, of postprandial plasma glucose and/or of glycosylated hemoglobin HbA1c;
  preventing, slowing, delaying or reversing progression from pre-diabetes, impaired glucose tolerance (IGT), impaired fasting blood glucose (IFG), insulin resistance and/or from metabolic syndrome to type 2 diabetes mellitus;
  preventing, reducing the risk of, slowing the progression of, delaying or treating of complications of diabetes mellitus such as micro- and macrovascular diseases, such as nephropathy, micro- or macroalbuminuria, proteinuria, retinopathy, cataracts, neuropathy, learning or memory impairment, neurodegenerative or cognitive disorders, cardio- or cerebrovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy, heart failure, heart rhythm disorders, vascular restenosis, and/or stroke;

reducing body weight and/or body fat and/or liver fat and/or intra-myocellular fat or preventing an increase in body weight and/or body fat and/or liver fat and/or intra-myocellular fat or facilitating a reduction in body weight and/or body fat and/or liver fat and/or intra-myocellular fat;

preventing, slowing, delaying or treating the degeneration of pancreatic beta cells and/or the decline of the functionality of pancreatic beta cells and/or for improving and/or restoring the functionality of pancreatic beta cells and/or stimulating and/or restoring or protecting the functionality of pancreatic insulin secretion;

preventing, slowing, delaying or treating non alcoholic fatty liver disease (NAFLD) including hepatic steatosis, non-alcoholic steatohepatitis (NASH) and/or liver fibrosis (such as e.g. preventing, slowing the progression, delaying, attenuating, treating or reversing hepatic steatosis, (hepatic) inflammation and/or an abnormal accumulation of liver fat);

preventing, slowing the progression of, delaying or treating type 2 diabetes with failure to conventional antidiabetic mono- or combination therapy;

achieving a reduction in the dose of conventional antidiabetic medication required for adequate therapeutic effect;

reducing the risk for adverse effects associated with conventional antidiabetic medication; and/or maintaining and/or improving the insulin sensitivity and/or for treating or preventing hyperinsulinemia and/or insulin resistance;

in a patient in need thereof (such as e.g a patient as described herein), said method comprising combined (e.g. simultaneous, separate or sequential) administration of a DPP-4 inhibitor as defined herein and a GLP-1 receptor agonist as defined herein.

In addition, the present invention relates to the combination according to this invention comprising a DPP-4 inhibitor as defined herein and a GLP-1 receptor agonist as defined herein for use in treating and/or preventing (including slowing the progression or delaying the onset) of metabolic diseases as defined herein, particularly diabetes (especially type 2 diabetes and obesity, or conditions related thereto, including diabetic complications), optionally in combination with one or more other therapeutic agents as described herein.

In addition, the present invention relates to the use of a combination according to this invention comprising a DPP-4 inhibitor as defined herein and a GLP-1 receptor agonist as defined herein for the manufacture of a medicament for use in a therapeutic method as described hereinbefore or hereinafter.

In addition, the present invention relates to a combination according to this invention comprising a DPP-4 inhibitor as defined herein and a GLP-1 receptor agonist as defined herein for use in a therapeutic method as described hereinbefore or hereinafter.

In addition, the present invention relates to a method of treating and/or preventing (including slowing the progression or delaying the onset) of a metabolic disease, particularly diabetes (especially type 2 diabetes or conditions related thereto, including diabetic complications) comprising administering to the patient in need thereof (such as e.g a patient as described herein) a combination according to this invention comprising a DPP-4 inhibitor as defined herein and a GLP-1 receptor agonist as defined herein.

In addition, the present invention relates to the use of a DPP-4 inhibitor as defined herein for the manufacture of a medicament for use in combination with a GLP-1 receptor agonist as defined herein for treating and/or preventing (including slowing the progression or delaying the onset) of metabolic diseases, particularly diabetes (especially type 2 diabetes and conditions related thereto, including diabetic complications).

In addition, the present invention relates to the use of a GLP-1 receptor agonist as defined herein for the manufacture of a medicament for use in combination with a DPP-4 inhibitor as defined herein for treating and/or preventing (including slowing the progression or delaying the onset) of metabolic diseases, particularly diabetes (especially type 2 diabetes and conditions related thereto, including diabetic complications).

In addition, the present invention relates a DPP-4 inhibitor as defined herein for use in a combination treatment according to the invention in a patient in need thereof (such as e.g a patient as described herein).

In addition, the present invention relates a GLP-1 receptor agonist as defined herein for use in a combination treatment according to the invention in a patient in need thereof (such as e.g a patient as described herein).

In addition, the present invention relates a DPP-4 inhibitor as defined herein, optionally in combination with one or more other active substances (such as e.g. metformin or pioglitazone), for use in a combination treatment according to the invention in a patient in need thereof.

In addition, the invention relates to a DPP-4 inhibitor as defined herein for use in a method as described hereinbefore or hereinafter, said method comprising administering the DPP-4 inhibitor, optionally in combination with one or more other active substances (e.g. which may selected from those mentioned herein, such as e.g. metformin or pioglitazone), to the patient.

In an embodiment, the present invention relates to a method for reducing and maintaining body weight and/or body fat in a patient in need thereof (particularly type 2 diabetes patient being obese or overweight) comprising administering a combination comprising a GLP-1 receptor agonist (e.g. GLP-1 or GLP-1 analogue as defined herein) and a DPP-4 inhibitor as defined herein to the patient.

In an embodiment, the present invention relates to a method for reducing and maintaining body weight and/or body fat in a patient in need thereof (particularly type 2 diabetes patient being obese or overweight) comprising i) inducing body weight and/or body fat loss (e.g. by diet, exercise and/or treatment with an anti-obesity or body weight reducing agent as described herein, particularly by administering an effective amount of the GLP-1 receptor agonist to the patient) and ii.) administering an effective amount of a certain DPP-4 inhibitor to the patient, wherein, optionally, said DPP-4 inhibitor may be used as replacement of the weight and/or fat loss treatment i) or as add-on or initial combination therapy with the weight and/or fat loss treatment i).

In a particular embodiment, the present invention relates to a DPP-4 inhibitor as defined herein, optionally in combination with one or more other therapeutic agents, for use in a method of preventing body weight and/or body fat gain or controlling, stabilizing or maintaining a reduced body weight and/or body fat after initial weight reducing treatment (such as e.g. diet, exercise and/or treatment with an anti-obesity or body weight reducing agent as described herein), particularly after discontinuation of initial treatment with a GLP-1 receptor agonist (e.g. GLP-1 or GLP-1 analogue as defined herein), in a patient in need thereof.

In a particular embodiment, the present invention relates to a method for reducing and maintaining body weight and/or body fat in a patient in need thereof (particularly type 2 diabetes patient being obese or overweight) comprising the combined (e.g. separate, simultaneous or sequential) administration of a GLP-1 receptor agonist (e.g. GLP-1 or GLP-1 analogue as defined herein) and a DPP-4 inhibitor as defined herein; preferably said method comprising the sequential administration of the GLP-1 receptor agonist followed by the DPP-4 inhibitor.

In a particular embodiment, the present invention relates to a method for reducing and maintaining body weight and/or body fat in a patient in need thereof (particularly type 2 diabetes patient being obese or overweight), said method comprising i) inducing body weight and/or body fat loss (e.g. by administering an effective amount of a GLP-1 receptor agonist (e.g. GLP-1 or GLP-1 analogue as defined herein) to the patient) and ii.) administering an effective amount of a DPP-4 inhibitor as defined herein to the patient for maintaining the body weight and/or body fat loss.

In a particular embodiment, the present invention relates to a method for reducing and maintaining body weight and/or body fat in a patient in need thereof (particularly type 2 diabetes patient being obese or overweight), said method comprising i) inducing initial body weight and/or body fat loss (e.g. by administering an effective amount of a GLP-1 receptor agonist (e.g. GLP-1 or GLP-1 analogue as defined herein) to the patient) and, subsequently, ii.) administering an effective amount of a DPP-4 inhibitor as defined herein to the patient, preferably thereby replacing the GLP-1 receptor agonist.

In a particular embodiment, the present invention relates to a DPP-4 inhibitor as defined herein for use in preventing of body weight and/or body fat gain or controlling, stabilizing or maintaining a reduced body weight and/or body fat after discontinuation of a weight reducing treatment (such as e.g. diet, exercise and/or treatment with an anti-obesity or body weight reducing agent as described herein), particularly after discontinuation of treatment with a GLP-1 receptor agonist (e.g. GLP-1 or GLP-1 analogue as defined herein), in a patient in need thereof (such as e.g a patient as described herein).

In a particular embodiment, the present invention relates to the use of a DPP-4 inhibitor as defined herein for the manufacture of a medicament for use in preventing of body weight and/or body fat gain or controlling, stabilizing or maintaining a reduced body weight and/or body fat after initial weight reducing treatment (such as e.g. using diet, exercise and/or treatment with an anti-obesity or body weight reducing agent as described herein), particularly after initial treatment with a GLP-1 receptor agonist (e.g. GLP-1 or GLP-1 analogue as defined herein).

In a particular embodiment, the present invention relates to a method of preventing body weight gain and/or body fat gain or controlling, stabilizing or maintaining a reduced body weight and/or body fat after initial weight reducing treatment (such as e.g. using diet, exercise and/or treatment with an anti-obesity or body weight reducing agent as described herein), particularly after initial treatment with a GLP-1 receptor agonist (e.g. GLP-1 or GLP-1 analogue as defined herein), said method comprising administering an effective amount of a DPP-4 inhibitor as defined herein to the patient in need thereof.

In a particular embodiment, the present invention relates to a certain DPP-4 inhibitor for use in a method of reducing and maintaining body weight and/or body fat, or of attenuating, preventing or treating rebound of body weight gain and/or body fat gain following discontinuation of body weight loss treatment (particularly following discontinuation of treatment with a GLP-1 receptor agonist), particularly in obesity patients with or without diabetes, said method comprising administering a certain DPP-4 inhibitor (particularly linagliptin) subsequent to the body weight loss treatment (particularly subsequent to the treatment with the GLP-1 receptor agonist), optionally in combination with one or more other therapeutic agents.

In alternative to the use of a GLP-1 receptor agonist (e.g. GLP-1 or GLP-1 analogue as defined herein), the initial weight and/or fat loss may also be induced by using diet, exercise and/or treatment with an anti-obesity or body weight reducing agent, such as e.g. one or more agents selected from sibutramine, a lipase inhibitor such as tetrahydrolipstatin (orlistat), alizyme (cetilistat), a cannabinoid receptor 1 antagonist (e.g. rimonabant), a MC4 receptor agonist, a NPY receptor agonist such as e.g. a NPY2 antagonist (e.g. velneperit), a 5HT2c receptor agonist (e.g. lorcaserin), a Ghrelin antagonist, Pyy 3-36, leptin, a DGAT-1 inhibitor, a noradrenaline-dopamine-5HT reuptake inhibitor (e.g. tesofensine), bupropion/naltrexone, bupropion/zonisamide, topiramate/phentermine and pramlintide/metreleptin; or a MCH antagonist, a CCK inhibitor, a FAS inhibitor, an ACC inhibitor, a SCD inhibitor, a beta3 adrenoreceptor agonist, a MTP inhibitor (e.g. lomitapide) or amylin or an amylin analogue (e.g. davalintide or pramlintide).

Within an embodiment of the combination therapy of this invention (e.g. for treating type 2 diabetes, obesity or both, or for reducing and maintaining body weight), the GLP-1 receptor agonist may be used for inducing (initial) body weight loss, and/or the DPP-4 inhibitor may be used for maintaining body weight loss.

Another embodiment of the combination therapy of this invention (e.g. for treating type 2 diabetes, obesity or both, or for reducing and maintaining body weight and/or body fat), refers to a method comprising
i) administering an effective amount of a GLP-1 receptor agonist to the patient, particularly for inducing body weight and/or body fat loss in the patient,
ii) withdrawing the GLP-1 receptor agonist from the patient, particularly after the body weight and/or body fat is reduced in the patient, and
iii) administering an effective amount of a DPP-4 inhibitor to the patient, particularly for delaying body weight and/or body fat gain and/or maintaining reduction in body weight and/or in body fat in the patient.

Another embodiment of the combination therapy of this invention refers to the use of a certain DPP-4 inhibitor (particularly linagliptin) subsequent to body weight loss, particularly subsequent to a GLP-1 receptor agonist, optionally in combination with one or more other therapeutic agents.

Other aspects of the present invention become apparent to the skilled person from the foregoing and following remarks (including the examples and claims).

The aspects of the present invention, in particular the pharmaceutical compounds, compositions, combinations, methods and uses, refer to DPP-4 inhibitors and/or GLP-1 receptor agonists as defined hereinbefore and hereinafter.

A DPP-4 inhibitor within the meaning of the present invention includes, without being limited to, any of those DPP-4 inhibitors mentioned hereinabove and hereinbelow, preferably orally active DPP-4 inhibitors.

An embodiment of this invention refers to a DPP-4 inhibitor for use in the treatment and/or prevention of metabolic diseases (particularly type 2 diabetes mellitus) in type 2 diabetes patients, wherein said patients further suffering from renal disease, renal dysfunction or renal impairment, particularly characterized in that said DPP-4 inhibitor is administered to said patients in the same dose levels as to patients with normal renal function, thus e.g. said DPP-4 inhibitor does not require downward dosing adjustment for impaired renal function.

For example, a DPP-4 inhibitor according to this invention (especially one which may be suited for patients with impaired renal function) may be such an oral DPP-4 inhibitor, which and whose active metabolites have preferably a relatively wide (e.g. about >100 fold) therapeutic window and/or, especially, that are primarily eliminated via hepatic metabolism or biliary excretion.

In more detailed example, a DPP-4 inhibitor according to this invention (especially one which may be suited for patients with impaired renal function) may be such an orally administered DPP-4 inhibitor, which has a relatively wide (e.g. >100 fold) therapeutic window and/or which fulfils one or more of the following pharmacokinetic properties (preferably at its therapeutic oral dose levels):

The DPP-4 inhibitor is substantially or mainly excreted via the liver (e.g. >80% or even >90% of the administered oral dose), and/or for which renal excretion represents no substantial or only a minor elimination pathway (e.g. <10%, preferably <7%, of the administered oral dose measured, for example, by following elimination of a radiolabelled carbon ($^{14}C$) substance oral dose);

The DPP-4 inhibitor is excreted mainly unchanged as parent drug (e.g. with a mean of >70%, or >80%, or, preferably, 90% of excreted radioactivity in urine and faeces after oral dosing of radiolabelled carbon ($^{14}C$) substance), and/or which is eliminated to a non-substantial or only to a minor extent via metabolism (e.g. <30%, or <20%, or, preferably, 10%);

The (main) metabolite(s) of the DPP-4 inhibitor is/are pharmacologically inactive. Such as e.g. the main metabolite does not bind to the target enzyme DPP-4 and, optionally, it is rapidly eliminated compared to the parent compound (e.g. with a terminal half-life of the metabolite of ≤20 h, or, preferably, ≤about 16 h, such as e.g. 15.9 h).

In one embodiment, the (main) metabolite in plasma (which may be pharmacologically inactive) of a DPP-4 inhibitor having a 3-amino-piperidin-1-yl substituent is such a derivative where the amino group of the 3-amino-piperidin-1-yl moiety is replaced by a hydroxyl group to form the 3-hydroxy-piperidin-1-yl moiety (e.g. the 3-(S)-hydroxy-piperidin-1-yl moiety, which is formed by inversion of the configuration of the chiral center).

Further properties of a DPP-4 inhibitor according to this invention may be one or more of the following: Rapid attainment of steady state (e.g. reaching steady state plasma levels (>90% of the steady state plasma concentration) between second and fifth day of treatment with therapeutic oral dose levels), little accumulation (e.g. with a mean accumulation ratio $R_{A,AUC} \leq 1.4$ with therapeutic oral dose levels), and/or preserving a long-lasting effect on DPP-4 inhibition, preferably when used once-daily (e.g. with almost complete (>90%) DPP-4 inhibition at therapeutic oral dose levels, >80% inhibition over a 24 h interval after once-daily intake of therapeutic oral drug dose), significant decrease in 2 h postprandial blood glucose excursions by ≥80% (already on first day of therapy) at therapeutic dose levels, and cumulative amount of unchanged parent compound excreted in urine on first day being below 1% of the administered dose and increasing to not more than about 3-6% in steady state.

Thus, for example, a DPP-4 inhibitor according to this invention may be characterized in that said DPP-4 inhibitor is excreted to a non-substantial or only to a minor extent (e.g. <10%, preferably <7% of administered oral dose) via the kidney (measured, for example, by following elimination of a radiolabelled carbon ($^{14}C$) substance oral dose).

Further, a DPP-4 inhibitor according to this invention may be characterized in that said DPP-4 inhibitor is excreted substantially or mainly via the liver or faeces (measured, for example, by following elimination of a radiolabelled carbon ($^{14}C$) substance oral dose).

Further, a DPP-4 inhibitor according to this invention may be characterized in that said DPP-4 inhibitor is excreted mainly unchanged as parent drug (e.g. with a mean of >70%, or >80%, or, preferably, 90% of excreted radioactivity in urine and faeces after oral dosing of radiolabelled carbon ($^{14}C$) substance), said DPP-4 inhibitor is eliminated to a non-substantial or only to a minor extent via metabolism, and/or the main metabolite of said DPP-4 inhibitor is pharmacologically inactive or has a relatively wide therapeutic window.

Further, a DPP-4 inhibitor according to this invention may be characterized in that said DPP-4 inhibitor does not significantly impair glomerular and/or tubular function of a type 2 diabetes patient with chronic renal insufficiency (e.g. mild, moderate or severe renal impairment or end stage renal disease), and/or said DPP-4 inhibitor does not require to be dose-adjusted in a type 2 diabetes patient with impaired renal function (e.g. mild, moderate or severe renal impairment or end stage renal disease).

Further, a DPP-4 inhibitor according to this invention may be characterized in that said DPP-4 inhibitor provides its minimally effective dose at that dose that results in >50% inhibition of DPP-4 activity at trough (24 h after last dose) in >80% of patients, and/or said DPP-4 inhibitor provides its fully therapeutic dose at that dose that results in >80% inhibition of DPP-4 activity at trough (24 h after last dose) in >80% of patients.

In a first embodiment (embodiment A), a DPP-4 inhibitor in the context of the present invention is any DPP-4 inhibitor of formula (I)

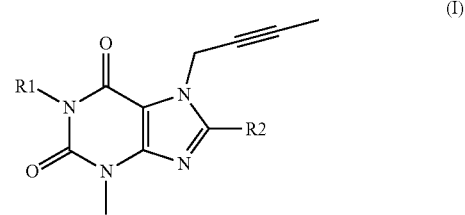

or formula (II)

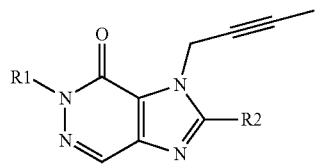

or formula (III)

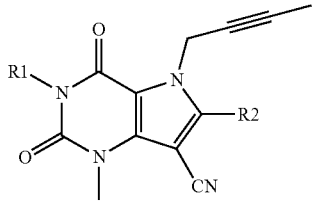

or formula (IV)

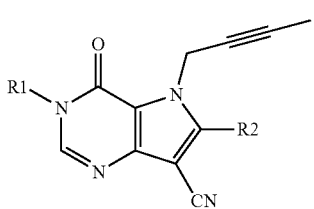

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino, or its pharmaceutically acceptable salt.

In a second embodiment (embodiment B), a DPP-4 inhibitor in the context of the present invention is a DPP-4 inhibitor selected from the group consisting of sitagliptin, vildagliptin, saxagliptin, alogliptin, gemigliptin,
(2S)-1-{[2-(5-Methyl-2-phenyl-oxazol-4-yl)-ethylamino]-acetyl}-pyrrolidine-2-carbonitrile,
(2S)-1-{[1,1,-Dimethyl-3-(4-pyridin-3-yl-imidazol-1-yl)-propylamino]-acetyl}-pyrrolidine-2-carbonitrile,
(S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one,
(3,3-Difluoropyrrolidin-1-yl)-((2S,4S)-4-(4-(pyrimidin-2-yl)piperazin-1-yl)pyrrolidin-2-yl)methanone,
(1 ((3S,4S)-4-amino-1-(4-(3,3-difluoropyrrolidin-1-yl)-1,3,5-triazin-2-yl)pyrrolidin-3-yl)-5,5-difluoropiperidin-2-one,
(2S,4S)-1-{2-[(3S,1R)-3-(1H-1,2,4-Triazol-1-ylmethyl)cyclopentylamino]-acetyl}-4-fluoropyrrolidine-2-carbonitrile,
(R)-2-[6-(3-Amino-piperidin-1-yl)-3-methyl-2,4-dioxo-3,4-dihydro-2H-pyrimidin-1-ylmethyl]-4-fluoro-benzonitrile,
5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide,
3-{(2S,4S)-4-[4-(3-Methyl-1-phenyl-1H-pyrazol-5-yl)piperazin-1-yl]pyrrolidin-2-ylcarbonyl}thiazolidine,
[(2R)-1-{[(3R)-pyrrolidin-3-ylamino]acetyl}pyrrolidin-2-yl]boronic acid,
(2S,4S)-1-[2-[(4-ethoxycarbonylbicyclo[2.2.2]oct-1-yl)amino]acetyl]-4-fluoropyrrolidine-2-carbonitrile,
2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile,
6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione, and
(S)-2-methylpyrazolo[1,5-a]primidine-6-carboxylic acid {2-[(2-cyanopyrrolidin-1-yl)-2-oxoethylamino]-2-methylpropyl}amide, or its pharmaceutically acceptable salt.

Regarding the first embodiment (embodiment A), preferred DPP-4 inhibitors are any or all of the following compounds and their pharmaceutically acceptable salts:

1-[(4-methyl-quinazolin-2-yl)methyl]-3-methyl-7-(2-butyn-1-yl)-8-(3-(R)-amino-piperidin-1-yl)-xanthine (compare WO 2004/018468, example 2(142)):

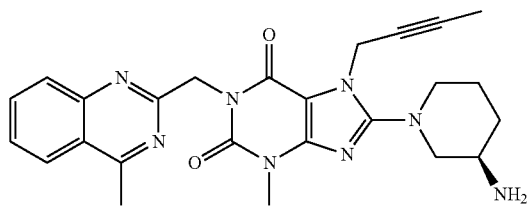 [SMILES: CC#CCn1c(N2CCC[C@@H](N)C2)nc2c1c(=O)n(Cc1nc(C)c3ccccc3n1)c(=O)n2C]

1-[([1,5]naphthyridin-2-yl)methyl]-3-methyl-7-(2-butyn-1-yl)-8-((R)-3-amino-piperidin-1-yl)-xanthine (compare WO 2004/018468, example 2(252)):

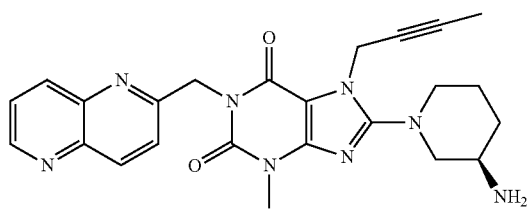 [SMILES: CC#CCn1c(N2CCC[C@@H](N)C2)nc2c1c(=O)n(Cc1ccc3ncccc3n1)c(=O)n2C]

1-[(Quinazolin-2-yl)methyl]-3-methyl-7-(2-butyn-1-yl)-8-((R)-3-amino-piperidin-1-yl)-xanthine (compare WO 2004/018468, example 2(80)):

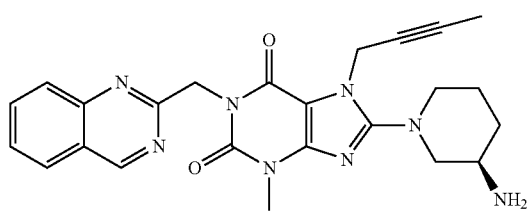 [SMILES: CC#CCn1c(N2CCC[C@@H](N)C2)nc2c1c(=O)n(Cc1ncc3ccccc3n1)c(=O)n2C]

2-((R)-3-Amino-piperidin-1-yl)-3-(but-2-yinyl)-5-(4-methyl-quinazolin-2-ylmethyl)-3,5-dihydro-imidazo[4,5-d]pyridazin-4-one (compare WO 2004/050658, example 136):

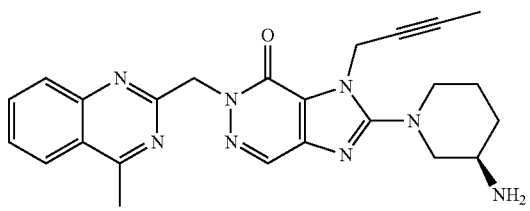 [SMILES: CC#CCn1c(N2CCC[C@@H](N)C2)nc2cnn(Cc3nc(C)c4ccccc4n3)c(=O)c21]

1-[(4-Methyl-quinazolin-2-yl)methyl]-3-methyl-7-(2-butyn-1-yl)-8-[(2-amino-2-methyl-propyl)-methylamino]-xanthine (compare WO 2006/029769, example 2(1)):

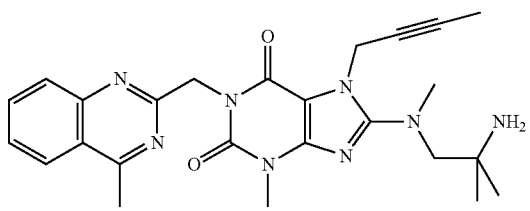 [SMILES: CC#CCn1c(N(C)CC(C)(C)N)nc2c1c(=O)n(Cc1nc(C)c3ccccc3n1)c(=O)n2C]

1-[(3-Cyano-quinolin-2-yl)methyl]-3-methyl-7-(2-butyn-1-yl)-8-((R)-3-amino-piperidin-1-yl)-xanthine (compare WO 2005/085246, example 1(30)):

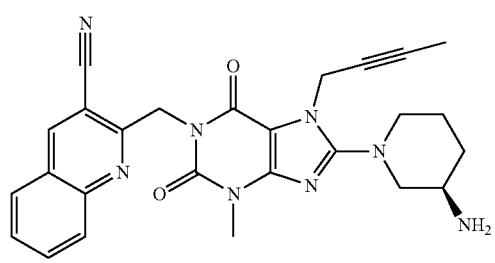 [SMILES: CC#CCn1c(N2CCC[C@@H](N)C2)nc2c1c(=O)n(Cc1nc3ccccc3cc1C#N)c(=O)n2C]

1-(2-Cyano-benzyl)-3-methyl-7-(2-butyn-1-yl)-8-((R)-3-amino-piperidin-1-yl)-xanthine (compare WO 2005/085246, example 1(39)):

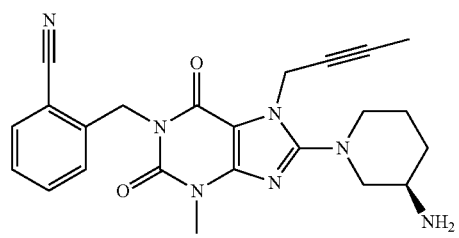 [SMILES: CC#CCn1c(N2CCC[C@@H](N)C2)nc2c1c(=O)n(Cc1ccccc1C#N)c(=O)n2C]

1-[(4-Methyl-quinazolin-2-yl)methyl]-3-methyl-7-(2-butyn-1-yl)-8-[(S)-(2-amino-propyl)-methylamino]-xanthine (compare WO 2006/029769, example 2(4)):

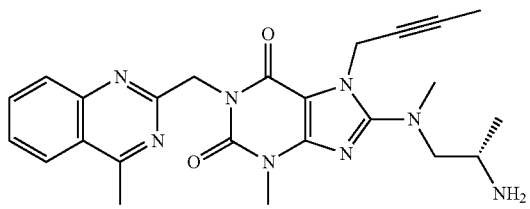 [SMILES: CC#CCn1c(N(C)C[C@H](C)N)nc2c1c(=O)n(Cc1nc(C)c3ccccc3n1)c(=O)n2C]

1-[(3-Cyano-pyridin-2-yl)methyl]-3-methyl-7-(2-butyn-1-yl)-8-((R)-3-amino-piperidin-1-yl)-xanthine (compare WO 2005/085246, example 1(52)):

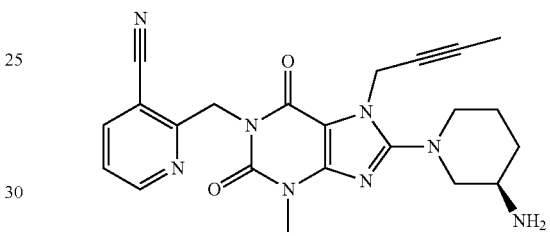

1-[(4-Methyl-pyrimidin-2-yl)methyl]-3-methyl-7-(2-butyn-1-yl)-8-((R)-3-amino-piperidin-1-yl)-xanthine (compare WO 2005/085246, example 1(81)):

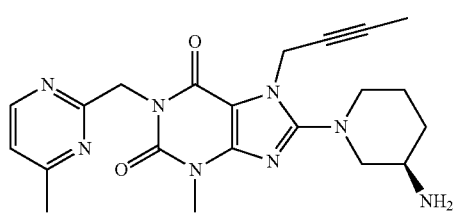 [SMILES: CC#CCn1c(N2CCC[C@@H](N)C2)nc2c1c(=O)n(Cc1nccc(C)n1)c(=O)n2C]

1-[(4,6-Dimethyl-pyrimidin-2-yl)methyl]-3-methyl-7-(2-butyn-1-yl)-8-((R)-3-amino-piperidin-1-yl)-xanthine (compare WO 2005/085246, example 1(82)):

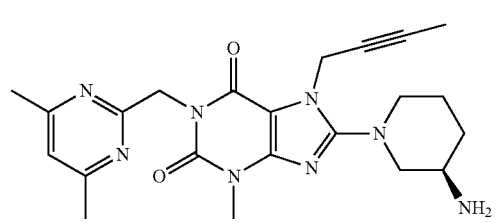 [SMILES: CC#CCn1c(N2CCC[C@@H](N)C2)nc2c1c(=O)n(Cc1nc(C)cc(C)n1)c(=O)n2C]

1-[(Quinoxalin-6-yl)methyl]-3-methyl-7-(2-butyn-1-yl)-8-((R)-3-amino-piperidin-1-yl)-xanthine (compare WO 2005/085246, example 1(83)):

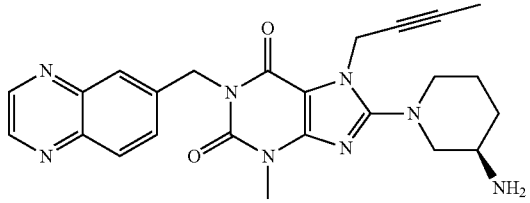 [SMILES: CC#CCn1c(N2CCC[C@@H](N)C2)nc2c1c(=O)n(Cc1ccc3nccnc3c1)c(=O)n2C]

These DPP-4 inhibitors are distinguished from structurally comparable DPP-4 inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

A more preferred DPP-4 inhibitor among the abovementioned DPP-4 inhibitors of embodiment A of this invention is 1-[(4-methyl-quinazolin-2-yl)methyl]-3-methyl-7-(2-butyn-1-yl)-8-(3-(R)-amino-piperidin-1-yl)-xanthine, particularly the free base thereof (which is also known as linagliptin or BI 1356).

As further DPP-4 inhibitors the following compounds can be mentioned:

Sitagliptin (MK-0431) having the structural formula A below is (3R)-3-amino-1-[3-(trifluoromethyl)-5,6,7,8-tetrahydro-5H-[1,2,4]triazolo[4,3-a]pyrazin-7-yl]-4-(2,4,5-trifluorophenyl)butan-1-one, also named (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine,

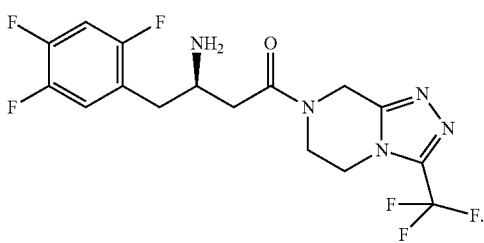

(A)

In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate. Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485.

For details, e.g. on a process to manufacture, to formulate or to use this compound or a salt thereof, reference is thus made to these documents.

A tablet formulation for sitagliptin is commercially available under the trade name Januvia®. A tablet formulation for sitagliptin/metformin combination is commercially available under the trade name Janumet®.

Vildagliptin (LAF-237) having the structural formula B below is (2S)-{[(3-hydroxyadamantan-1-yl)amino]acetyl}pyrrolidine-2-carbonitrile, also named (S)-1-[(3-hydroxy-1-adamantyl)amino]acetyl-2-cyano-pyrrolidine,

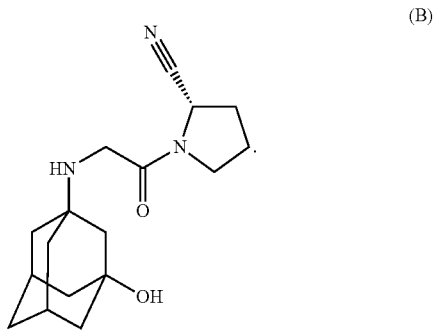 [SMILES: N#C[C@@H]1CCCN1C(=O)CNC12CC3CC(CC(O)(C3)C1)C2]

(B)

Vildagliptin is specifically disclosed in U.S. Pat. No. 6,166,063 and in Example 1 of WO 00/34241. Specific salts of vildagliptin are disclosed in WO 2007/019255. A crystalline form of vildagliptin as well as a vildagliptin tablet formulation are disclosed in WO 2006/078593. Vildagliptin can be formulated as described in WO 00/34241 or in WO 2005/067976. A modified release vildagliptin formulation is described in WO 2006/135723.

For details, e.g. on a process to manufacture, to formulate or to use this compound or a salt thereof, reference is thus made to these documents.

A tablet formulation for vildagliptin is expected to be commercially available under the trade name Galvus®. A tablet formulation for vildagliptin/metformin combination is commercially available under the trade name Eucreas®.

Saxagliptin (BMS-477118) having the structural formula C below is (1 S,3S,5S)-2-{(2S)-2-amino-2-(3-hydroxyadamantan-1-yl)acetyl}-2-azabicyclo[3.1.0]hexane-3-carbonitrile, also named (S)-3-hydroxyadamantylglycine-L-cis-4,5-methanoprolinenitrile,

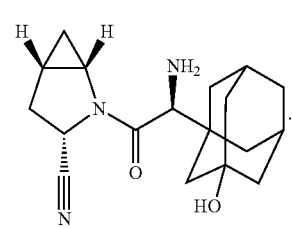

(C)

Saxagliptin is specifically disclosed in U.S. Pat. No. 6,395,767 and in Example 60 of WO 01/68603.

In one embodiment, saxagliptin is in the form of its HCl salt or its mono-benzoate salt as disclosed in WO 2004/052850. In a further embodiment, saxagliptin is in the form of the free base. In a yet further embodiment, saxagliptin is in the form of the monohydrate of the free base as disclosed in WO 2004/052850. Crystalline forms of the HCl salt and of the free base of saxagliptin are disclosed in WO 2008/131149. A process for preparing saxagliptin is also disclosed in WO 2005/106011 and WO 2005/115982. Saxagliptin can be formulated in a tablet as described in WO 2005/117841.

For details, e.g. on a process to manufacture, to formulate or to use this compound or a salt thereof, reference is thus made to these documents.

Alogliptin (SYR-322) having the structural formula E below is 2-({6-[(3R)-3-aminopiperidin-1-yl]-3-methyl-2,4-dioxo-3,4-dihydro-2H-pyrimidin-1-yl}methyl)benzonitrile

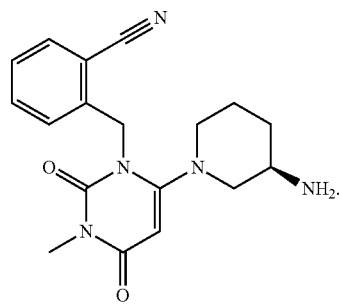

(E)

Alogliptin is specifically disclosed in US 2005/261271, EP 1586571 and in WO 2005/095381. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/112368 and, specifically, in WO 2007/035629. Alogliptin (namely its benzoate salt) can be formulated in a tablet and administered as described in WO 2007/033266. A solid preparation of alogliptin/pioglitazone and its preparation and use is described in WO 2008/093882. A solid preparation of alogliptin/metformin and its preparation and use is described in WO 2009/011451.

For details, e.g. on a process to manufacture, to formulate or to use this compound or a salt thereof, reference is thus made to these documents.

(2S)-1-{[2-(5-Methyl-2-phenyl-oxazol-4-yl)-ethylamino]-acetyl}-pyrrolidine-2-carbonitrile or a pharmaceutically acceptable salt thereof, preferably the mesylate, or (2S)-1-{[1,1,-Dimethyl-3-(4-pyridin-3-yl-imidazol-1-yl)-propylamino]-acetyl}-pyrrolidine-2-carbonitrile or a pharmaceutically acceptable salt thereof:

These compounds and methods for their preparation are disclosed in WO 03/037327. The mesylate salt of the former compound as well as crystalline polymorphs thereof are disclosed in WO 2006/100181. The fumarate salt of the latter compound as well as crystalline polymorphs thereof are disclosed in WO 2007/071576. These compounds can be formulated in a pharmaceutical composition as described in WO 2007/017423.

For details, e.g. on a process to manufacture, to formulate or to use these compounds or salts thereof, reference is thus made to these documents.

(S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one (also named carmegliptin) or a pharmaceutically acceptable salt thereof:

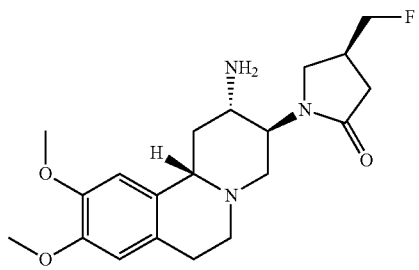 [SMILES: COc1cc2c(cc1OC)[C@@H]1C[C@H](N)[C@@H](N3C[C@@H](CF)CC3=O)CN1CC2]

This compound and methods for its preparation are disclosed in WO 2005/000848. A process for preparing this compound (specifically its dihydrochloride salt) is also disclosed in WO 2008/031749, WO 2008/031750 and WO 2008/055814. This compound can be formulated in a pharmaceutical composition as described in WO 2007/017423.

For details, e.g. on a process to manufacture, to formulate or to use this compound or a salt thereof, reference is thus made to these documents.

(3,3-Difluoropyrrolidin-1-yl)-((2S,4S)-4-(4-(pyrimidin-2-yl)piperazin-1-yl)pyrrolidin-2-yl)methanone (also named gosogliptin) or a pharmaceutically acceptable salt thereof:

This compound and methods for its preparation are disclosed in WO 2005/116014 and U.S. Pat. No. 7,291,618.

For details, e.g. on a process to manufacture, to formulate or to use this compound or a salt thereof, reference is thus made to these documents.

(1 ((3S,4S)-4-amino-1-(4-(3,3-difluoropyrrolidin-1-yl)-1,3,5-triazin-2-yl)pyrrolidin-3-yl)-5,5-difluoropiperidin-2-one or a pharmaceutically acceptable salt thereof:

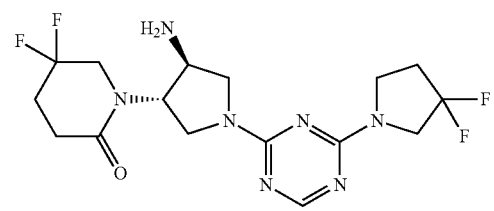 [SMILES: N[C@H]1CN(c2ncnc(N3CCC(F)(F)C3)n2)C[C@@H]1N1CC(F)(F)CCC1=O]

This compound and methods for its preparation are disclosed in WO 2007/148185 and US 20070299076. For details, e.g. on a process to manufacture, to formulate or to use this compound or a salt thereof, reference is thus made to these documents.

(2S,4S)-1-{2-[(3S,1R)-3-(1H-1,2,4-Triazol-1-ylmethyl)cyclopentylamino]-acetyl}-4-fluoropyrrolidine-2-carbonitrile (also named melogliptin) or a pharmaceutically acceptable salt thereof:

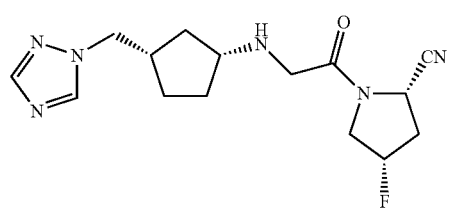 [SMILES: N#C[C@@H]1C[C@H](F)CN1C(=O)CN[C@@H]1CC[C@H](Cn2cncn2)C1]

This compound and methods for its preparation are disclosed in WO 2006/040625 and WO 2008/001195. Specifically claimed salts include the methanesulfonate and p-toluenesulfonate. For details, e.g. on a process to manufacture, to formulate or to use this compound or a salt thereof, reference is thus made to these documents.

(R)-2-[6-(3-Amino-piperidin-1-yl)-3-methyl-2,4-dioxo-3,4-dihydro-2H-pyrimidin-1-ylmethyl]-4-fluoro-benzonitrile or a pharmaceutically acceptable salt thereof:

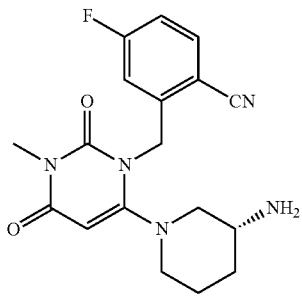 [SMILES: Cn1c(=O)cc(N2CCC[C@@H](N)C2)n(Cc2cc(F)ccc2C#N)c1=O]

This compound and methods for its preparation and use are disclosed in WO 2005/095381, US 2007060530, WO 2007/033350, WO 2007/035629, WO 2007/074884, WO 2007/112368, WO 2008/033851, WO 2008/114800 and WO 2008/114807. Specifically claimed salts include the succinate (WO 2008/067465), benzoate, benzenesulfonate, p-toluenesulfonate, (R)-mandelate and hydrochloride. For details, e.g. on a process to manufacture, to formulate or to use this compound or a salt thereof, reference is thus made to these documents.

5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide or a pharmaceutically acceptable salt thereof:

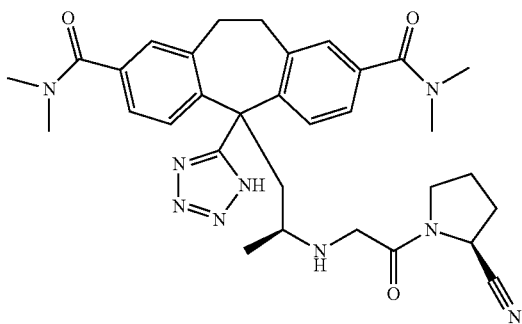 [SMILES: C[C@@H](CC1(c2nnn[nH]2)c2ccc(C(=O)N(C)C)cc2CCc2cc(C(=O)N(C)C)ccc21)NCC(=O)N1CCC[C@H]1C#N]

This compound and methods for its preparation are disclosed in WO 2006/116157 and US 2006/270701. For details, e.g. on a process to manufacture, to formulate or to use this compound or a salt thereof, reference is thus made to these documents.

3-{(2S,4S)-4-[4-(3-Methyl-1-phenyl-1H-pyrazol-5-yl)piperazin-1-yl]pyrrolidin-2-ylcarbonyl}thiazolidine (also named teneligliptin) or a pharmaceutically acceptable salt thereof:

This compound and methods for its preparation are disclosed in WO 02/14271. Specific salts are disclosed in WO 2006/088129 and WO 2006/118127 (including hydrochloride, hydrobromide, inter alia). Combination therapy using this compound is described in WO 2006/129785. For details, e.g. on a process to manufacture, to formulate or to use this compound or a salt thereof, reference is thus made to these documents.

[(2R)-1-{[(3R)-pyrrolidin-3-ylamino]acetyl}pyrrolidin-2-yl]boronic acid (also named dutogliptin) or a pharmaceutically acceptable salt thereof:

This compound and methods for its preparation are disclosed in WO 2005/047297, WO 2008/109681 and WO 2009/009751. Specific salts are disclosed in WO 2008/027273 (including citrate, tartrate). A formulation of this compound is described in WO 2008/144730. A formulation of dutogliptin (as its tartrate salt) with metformin is described in WO 2009/091663. For details, e.g. on a process to manufacture, to formulate or to use this compound or a salt thereof, reference is thus made to these documents.

(2S,4S)-1-[2-[(4-ethoxycarbonylbicyclo[2.2.2]oct-1-yl)amino]acetyl]-4-fluoropyrrolidine-2-carbonitrile (also named besigliptin) or a pharmaceutically acceptable salt thereof:

This compound and methods for its preparation are disclosed in WO 2005/075421, US 2008/146818 and WO 2008/114857. For details, e.g. on a process to manufacture, to formulate or to use this compound or a salt thereof, reference is thus made to these documents.

2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile or a pharmaceutically acceptable salt thereof, or 6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione or a pharmaceutically acceptable salt thereof:

These compounds and methods for their preparation are disclosed in WO 2009/084497 and WO 2006/068163, respectively. Combination therapy using the latter of these two compounds is described in WO 2009/128360. For details, e.g. on a process to manufacture, to formulate or to use these compounds or salts thereof, reference is thus made to these documents.

(S)-2-methylpyrazolo[1,5-a]primidine-6-carboxylic acid {2-[(2-cyanopyrrolidin-1-yl)-2-oxoethylamino]-2-methylpropyl}amide (also named anagliptin) or a pharmaceutically acceptable salt:

This compound and methods for its preparation are disclosed in WO 2004/067509. Combination therapy using this compound is described in WO 2009/139362. For details, e.g. on a process to manufacture, to formulate or to use this compound or a salt thereof, reference is thus made to these documents.

Preferably the DPP-4 inhibitor of this invention is selected from the group (group G1) consisting of linagliptin, sitagliptin, vildagliptin, alogliptin, saxagliptin, teneligliptin and dutogliptin, or a pharmaceutically acceptable salt of one of the hereinmentioned DPP-4 inhibitors, or a prodrug thereof.

In another embodiment, the DPP-4 inhibitor of this invention is selected from the group (group H1) consisting of linagliptin, sitagliptin, vildagliptin, alogliptin, saxagliptin, teneligliptin, anagliptin, gemigliptin and dutogliptin, or a pharmaceutically acceptable salt of one of the hereinmentioned DPP-4 inhibitors, or a prodrug thereof.

A particularly preferred DPP-4 inhibitor within the present invention is linagliptin. The term "linagliptin" as employed herein refers to linagliptin or a pharmaceutically acceptable salt thereof, including hydrates and solvates thereof, and crystalline forms thereof, preferably linagliptin refers to 1-[(4-methyl-quinazolin-2-yl)methyl]-3-methyl-7-(2-butyn-1-yl)-8-(3-(R)-amino-piperidin-1-yl)-xanthine. Crystalline forms are described in WO 2007/128721. Methods for the manufacture of linagliptin are described in the patent applications WO 2004/018468 and WO 2006/048427 for example. Linagliptin is distinguished from structurally comparable DPP-4 inhibitors, as it combines exceptional potency and a long-lasting effect with favourable pharmacological properties, receptor selectivity and a favourable side-effect profile or bring about unexpected therapeutic advantages or improvements in mono- or dual or triple combination therapy.

For avoidance of any doubt, the disclosure of each of the foregoing and following documents cited above in connection with the specified DPP-4 inhibitors is specifically incorporated herein by reference in its entirety.

GLP-1 receptor agonists include, without being limited, exogenous GLP-1 (natural or synthetic), GLP-1 analogues (including longer acting analogues which are resistant to or have reduced susceptibility to enzymatic degradation by DPP-4 and NEP 24.11) and other substances (whether peptidic or non-peptidic, e.g. small molecules) which promote signalling through the GLP-1 receptor.

Examples of GLP-1 analogues may include (group G2): exenatide (synthetic exendin-4, e.g. formulated as Byetta); exenatide LAR (long acting release formulation of exenatide, e.g. formulated as Bydureon); liraglutide (e.g. formulated as Victoza); taspoglutide; semaglutide; albiglutide (e.g. formulated as Syncria); lixisenatide; dulaglutide; and the di-PEGylated GLP-1 compound comprising the amino acid sequence of the pegylated compound of Formula I (SEQ ID NO:1) according to WO 2006/124529 (the disclosure of which is incorporated herein), wherein $Xaa_8$ is Val, $Xaa_{22}$ is Glu, $Xaa_{33}$ is Ile, and $Xaa_{46}$ is Cys-NH$_2$, and wherein one PEG molecule is covalently attached to $Cys_{45}$ and one PEG molecule is covelently attached to $Cys_{46}$-NH$_2$, wherein each of the PEG molecules used for PEGylation reaction is a 20,000 dalton linear methoxy PEG maleimide (preferably the GLP-1 derivative consists of the amino acid sequence of $Val^8$-$Glu^{22}$-$Ile^{33}$-Cys-NH$_2^{46}$-GLP-1 (SEQ ID NO: 1) (cf. SEQ ID NO:21 of WO 2009/020802, the disclosure of which is incorporated herein).

Preferred examples of GLP-1 receptor agonists (GLP-1 analogues) of this invention are exenatide, exenatide LAR, liraglutide, taspoglutide, semaglutide, albiglutide, lixisenatide and dulaglutide.

GLP-1 analogues have typically significant sequence identity to GLP-1 (e.g. greater than 50%, 75%, 90% or 95%) and may be derivatised, e.g. by conjunction to other proteins (e.g. albumin or IgG-Fc fusion protein) or through chemical modification.

Unless otherwise noted, according to this invention it is to be understood that the definitions of the active agents (including the DPP-4 inhibitors and GLP-1 receptor agonists) mentioned hereinabove and hereinbelow may also contemplate their pharmaceutically acceptable salts, and prodrugs, hydrates, solvates and polymorphic forms thereof. Particularly the terms of the therapeutic agents given herein refer to the respective active drugs. With respect to salts, hydrates and polymorphic forms thereof, particular reference is made to those which are referred to herein.

In an embodiment the combinations, compositions, methods and uses according to this invention relate to combinations wherein the DPP-4 inhibitor and the GLP-1 receptor agonist are preferably selected according to the entries in the Table 1:

TABLE 1

| DPP-4 Inhibitor | GLP-1 receptor agonist |
| --- | --- |
| selected from embodiment B | selected from group G2 |
| selected from embodiment B | exenatide |

TABLE 1-continued

| DPP-4 Inhibitor | GLP-1 receptor agonist |
| --- | --- |
| selected from embodiment B | exenatide LAR |
| selected from embodiment B | liraglutide |
| selected from embodiment B | taspoglutide |
| selected from embodiment B | semaglutide |
| selected from embodiment B | albiglutide |
| selected from embodiment B | lixisenatide |
| selected from embodiment B | dulaglutide |
| selected from group G1 | selected from group G2 |
| selected from group G1 | exenatide |
| selected from group G1 | exenatide LAR |
| selected from group G1 | liraglutide |
| selected from group G1 | taspoglutide |
| selected from group G1 | semaglutide |
| selected from group G1 | albiglutide |
| selected from group G1 | lixisenatide |
| selected from group G1 | dulaglutide |
| linagliptin | exenatide |
| linagliptin | exenatide LAR |
| linagliptin | liraglutide |
| linagliptin | taspoglutide |
| linagliptin | semaglutide |
| linagliptin | albiglutide |
| linagliptin | lixisenatide |
| linagliptin | dulaglutide |
| linagliptin | selected from group G2 |

In a particular embodiment (embodiment E) the combinations, compositions, methods and uses according to this invention relate to combinations wherein the DPP-4 inhibitor is linagliptin. According to this particular embodiment (embodiment E) the GLP-1 receptor agonist is preferably selected according to the entries E1 to E8 in the Table 2:

TABLE 2

| Embodiment | GLP-1 receptor agonist |
| --- | --- |
| E1 | exenatide |
| E2 | exenatide LAR |
| E3 | liraglutide |
| E4 | taspoglutide |
| E5 | semaglutide |
| E6 | albiglutide |
| E7 | lixisenatide |
| E8 | dulaglutide |

Within this invention it is to be understood that the combinations, compositions or combined uses according to this invention may envisage the simultaneous, sequential or separate administration of the active components or ingredients.

In this context, "combination" or "combined" within the meaning of this invention may include, without being limited, fixed and non-fixed (e.g. free) forms (including kits) and uses, such as e.g. the simultaneous, sequential or separate use of the components or ingredients.

The present invention also provides a kit-of-parts or combination therapeutic product comprising a) a pharmaceutical composition comprising a DPP-4 inhibitor as defined herein, optionally together with one or more pharmaceutically acceptable carriers and/or diluents, and b) a pharmaceutical composition comprising a GLP-1 receptor agonist as defined herein.

The present invention also provides a kit comprising
a) a DPP-4 inhibitor as defined herein, and
b) a GLP-1 receptor agonist as defined herein,
and, optionally, instructions directing use of the DPP-4 inhibitor and the GLP-1 receptor agonist in combination (e.g. simultaneously, separately, sequentially or chronologically staggered), e.g. for a purpose of this invention, such as e.g. for the treatment of type 2 diabetes, obesity and/or overweight, and/or for reducing and maintaining body weight in a (human) patient.

The combined administration of this invention may take place by administering the active components or ingredients together, such as e.g. by administering them simultaneously in one single or in two separate formulations or dosage forms. Alternatively, the administration may take place by administering the active components or ingredients sequentially, such as e.g. successively in two separate formulations or dosage forms.

For the combination therapy of this invention the active components or ingredients may be administered separately (which implies that they are formulated separately) or formulated altogether (which implies that they are formulated in the same preparation or in the same dosage form). Hence, the administration of one element of the combination of the present invention may be prior to, concurrent to, or subsequent to the administration of the other element of the combination. Preferably, for the combination therapy according to this invention the DPP-4 inhibitor and the GLP-1 receptor agonist are administered in different formulations.

Unless otherwise noted, combination therapy may refer to first line, second line or third line therapy, or initial or add-on combination therapy or replacement therapy.

With respect to embodiment A, the methods of synthesis for the DPP-4 inhibitors according to embodiment A of this invention are known to the skilled person. Advantageously, the DPP-4 inhibitors according to embodiment A of this invention can be prepared using synthetic methods as described in the literature. Thus, for example, purine derivatives of formula (I) can be obtained as described in WO 2002/068420, WO 2004/018468, WO 2005/085246, WO 2006/029769 or WO 2006/048427, the disclosures of which are incorporated herein. Purine derivatives of formula (II) can be obtained as described, for example, in WO 2004/050658 or WO 2005/110999, the disclosures of which are incorporated herein. Purine derivatives of formula (II) and (IV) can be obtained as described, for example, in WO 2006/068163, WO 2007/071738 or WO 2008/017670, the disclosures of which are incorporated herein. The preparation of those DPP-4 inhibitors, which are specifically mentioned hereinabove, is disclosed in the publications mentioned in connection therewith.

Polymorphous crystal modifications and formulations of particular DPP-4 inhibitors are disclosed in WO 2007/128721 and WO 2007/128724, respectively, the disclosures of which are incorporated herein in their entireties. Formulations of particular DPP-4 inhibitors with metformin or other combination partners are described in WO 2009/121945, the disclosure of which is incorporated herein in its entirety.

Typical dosage strengths of the dual fixed combination (tablet) of linagliptin/metformin IR (immediate release) are 2.5/500 mg, 2.5/850 mg and 2.5/1000 mg, which may be administered 1-3 times a day, particularly twice a day.

Typical dosage strengths of the dual fixed combination (tablet) of linagliptin/metformin XR (extended release) are 5/500 mg, 5/1000 mg and 5/1500 mg, or 2.5/500 mg, 2.5/750 mg and 2.5/1000 mg (each two tablets), which may be administered 1-2 times a day, particularly once a day, preferably to be taken in the evening with meal.

The present invention further provides a DPP-4 inhibitor as defined herein for use in (add-on or initial) combination therapy with metformin (e.g. in a total daily amount from 500 to 2000 mg metformin hydrochloride, such as e.g. 500 mg, 850 mg or 1000 mg once or twice daily).

With respect to embodiment B, the methods of synthesis for the DPP-4 inhibitors of embodiment B are described in the scientific literature and/or in published patent documents, particularly in those cited herein.

Suitable doses and dosage forms of the DPP-4 inhibitors may be determined by a person skilled in the art and may include those described herein or in the relevant references.

For pharmaceutical application in warm-blooded vertebrates, particularly humans, the compounds of this invention are usually used in dosages from 0.001 to 100 mg/kg body weight, preferably at 0.1-15 mg/kg, in each case 1 to 4 times a day. For this purpose, the compounds, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The pharmaceutical compositions according to this invention comprising the DPP-4 inhibitors as defined herein are thus prepared by the skilled person using pharmaceutically acceptable formulation excipients as described in the art. Examples of such excipients include, without being restricted to diluents, binders, carriers, fillers, lubricants, flow promoters, crystallisation retardants, disintegrants, solubilizers, colorants, pH regulators, surfactants and emulsifiers.

Examples of suitable diluents for compounds according to embodiment A include cellulose powder, calcium hydrogen phosphate, erythritol, low substituted hydroxypropyl cellulose, mannitol, pregelatinized starch or xylitol.

Examples of suitable lubricants for compounds according to embodiment A include talc, polyethyleneglycol, calcium behenate, calcium stearate, hydrogenated castor oil or magnesium stearate.

Examples of suitable binders for compounds according to embodiment A include copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, or low-substituted hydroxypropylcellulose (L-HPC).

Examples of suitable disintegrants for compounds according to embodiment A include corn starch or crospovidone.

Suitable methods of preparing pharmaceutical formulations of the DPP-4 inhibitors according to embodiment A of the invention are
  direct tabletting of the active substance in powder mixtures with suitable tabletting excipients;
  granulation with suitable excipients and subsequent mixing with suitable excipients and subsequent tabletting as well as film coating; or
  packing of powder mixtures or granules into capsules.
Suitable granulation methods are
  wet granulation in the intensive mixer followed by fluidised bed drying;
  one-pot granulation;
  fluidised bed granulation; or
  dry granulation (e.g. by roller compaction) with suitable excipients and subsequent tabletting or packing into capsules.

An exemplary composition (e.g. tablet core) of a DPP-4 inhibitor according to embodiment A of the invention comprises the first diluent mannitol, pregelatinized starch as a second diluent with additional binder properties, the binder copovidone, the disintegrant corn starch, and magnesium stearate as lubricant; wherein copovidone and/or corn starch may be optional.

A tablet of a DPP-4 inhibitor according to embodiment A of the invention may be film coated, preferably the film coat comprises hydroxypropylmethylcellulose (HPMC), polyethylene glycol (PEG), talc, titanium dioxide and iron oxide (e.g. red and/or yellow).

For details on dosage forms, formulations and administration of DPP-4 inhibitors of this invention and/or GLP-1 receptor agonists of this invention, reference is made to scientific literature and/or published patent documents, particularly to those cited herein.

In a preferred embodiment the element DPP-4 inhibitor of the combination according to the invention is preferably administered orally. In another preferred embodiment the component GLP-1 receptor agonist of the combination is preferably administered by injection.

Injectable formulations of the GLP-1 receptor agonists of this invention may be prepared according to known formulation techniques, e.g. using suitable liquid carriers, which usually comprise sterile water, and, optionally, further additives e.g. for aiding solubility or for preservation or the like, to obtain injectable solutions or suspensions.

The pharmaceutical compositions (or formulations) may be packaged in a variety of ways. Generally, an article for distribution includes a container that contains the pharmaceutical composition in an appropriate form. Tablets are typically packed in an appropriate primary package for easy handling, distribution and storage and for assurance of proper stability of the composition at prolonged contact with the environment during storage. Primary containers for tablets may be bottles or blister packs.

A suitable bottle, e.g. for a pharmaceutical composition or combination comprising a DPP-4 inhibitor according to embodiment A of the invention, may be made from glass or polymer (preferably polypropylene (PP) or high density polyethylene (HD-PE)) and sealed with a screw cap. The screw cap may be provided with a child resistant safety closure (e.g. press-and-twist closure) for preventing or hampering access to the contents by children. If required (e.g. in regions with high humidity), by the additional use of a desiccant (such as e.g. bentonite clay, molecular sieves, or, preferably, silica gel) the shelf life of the packaged composition can be prolonged.

A suitable blister pack, e.g. for a pharmaceutical composition or combination comprising a DPP-4 inhibitor according to embodiment A of the invention, comprises or is formed of a top foil (which is breachable by the tablets) and a bottom part (which contains pockets for the tablets). The top foil may contain a metalic foil, particularly an aluminium or aluminium alloy foil (e.g. having a thickness of 20 μm to 45 μm, preferably 20 μm to 25 μm) that is coated with a heat-sealing polymer layer on its inner side (sealing side). The bottom part may contain a multi-layer polymer foil (such as e.g. poly(vinyl choride) (PVC) coated with poly(vinylidene choride) (PVDC); or a PVC foil laminated with poly(chlorotriflouroethylene) (PCTFE)) or a multi-layer polymer-metal-polymer foil (such as e.g. a cold-formable laminated PVC/aluminium/polyamide composition).

To ensure a long storage period especially under hot and wet climate conditions an additional overwrap or pouch made of a multi-layer polymer-metal-polymer foil (e.g. a laminated polyethylene/aluminium/polyester composition) may be used for the blister packs. Supplementary desiccant (such as e.g. bentonite clay, molecular sieves, or, preferably, silica gel) in this pouch package may prolong the shelf life even more under such harsh conditions.

The article may further comprise a label or package insert, which refer to instructions customarily included in commercial packages of therapeutic products, that may contain information about the indications, usage, dosage, administration, contraindications and/or warnings concerning the use of such therapeutic products. In one embodiment, the label or package inserts indicates that the composition can be used for any of the purposes described herein.

With respect to the first embodiment (embodiment A), the dosage typically required of the DPP-4 inhibitors mentioned herein in embodiment A when administered intravenously is 0.1 mg to 10 mg, preferably 0.25 mg to 5 mg, and when administered orally is 0.5 mg to 100 mg, preferably 2.5 mg to 50 mg or 0.5 mg to 10 mg, more preferably 2.5 mg to 10 mg or 1 mg to 5 mg, in each case 1 to 4 times a day. Thus, e.g. the dosage of 1-[(4-methyl-quinazolin-2-yl)methyl]-3-methyl-7-(2-butyn-1-yl)-8-(3-(R)-amino-piperidin-1-yl)-xanthine when administered orally is 0.5 mg to 10 mg per patient per day, preferably 2.5 mg to 10 mg or 1 mg to 5 mg per patient per day.

A dosage form prepared with a pharmaceutical composition comprising a DPP-4 inhibitor mentioned herein in embodiment A contain the active ingredient in a dosage range of 0.1-100 mg. Thus, e.g. particular dosage strengths of 1-[(4-methyl-quinazolin-2-yl)methyl]-3-methyl-7-(2-butyn-1-yl)-8-(3-(R)-amino-piperidin-1-yl)-xanthine are 0.5 mg, 1 mg, 2.5 mg, 5 mg and 10 mg.

With respect to the second embodiment (embodiment B), the doses of DPP-4 inhibitors mentioned herein in embodiment B to be administered to mammals, for example human beings, of, for example, approximately 70 kg body weight, may be generally from about 0.5 mg to about 350 mg, for example from about 10 mg to about 250 mg, preferably 20-200 mg, more preferably 20-100 mg, of the active moiety per person per day, or from about 0.5 mg to about 20 mg, preferably 2.5-10 mg, per person per day, divided preferably into 1 to 4 single doses which may, for example, be of the same size. Single dosage strengths comprise, for example, 10, 25, 40, 50, 75, 100, 150 and 200 mg of the DPP-4 inhibitor active moiety.

A dosage strength of the DPP-4 inhibitor sitagliptin is usually between 25 and 200 mg of the active moiety. A recommended dose of sitagliptin is 100 mg calculated for the active moiety (free base anhydrate) once daily. Unit dosage strengths of sitagliptin free base anhydrate (active moiety) are 25, 50, 75, 100, 150 and 200 mg. Particular unit dosage strengths of sitagliptin (e.g. per tablet) are 25, 50 and 100 mg. An equivalent amount of sitagliptin phosphate monohydrate to the sitagliptin free base anhydrate is used in the pharmaceutical compositions, namely, 32.13, 64.25, 96.38, 128.5, 192.75, and 257 mg, respectively. Adjusted dosages of 25 and 50 mg sitagliptin are used for patients with renal failure. Typical dosage strengths of the dual combination of sitagliptin/metformin are 50/500 mg and 50/1000 mg.

A dosage range of the DPP-4 inhibitor vildagliptin is usually between 10 and 150 mg daily, in particular between 25 and 150 mg, 25 and 100 mg or 25 and 50 mg or 50 and 100 mg daily. Particular examples of daily oral dosage are 25, 30, 35, 45, 50, 55, 60, 80, 100 or 150 mg. In a more particular aspect, the daily administration of vildagliptin may be between 25 and 150 mg or between 50 and 100 mg.

In another more particular aspect, the daily administration of vildagliptin may be 50 or 100 mg. The application of the active ingredient may occur up to three times a day, preferably one or two times a day. Particular dosage strengths are 50 mg or 100 mg vildagliptin. Typical dosage strengths of the dual combination of vildagliptin/metformin are 50/850 mg and 50/1000 mg.

Alogliptin may be administered to a patient at a daily dose of between 5 mg/day and 250 mg/day, optionally between 10 mg and 200 mg, optionally between 10 mg and 150 mg, and optionally between 10 mg and 100 mg of alogliptin (in each instance based on the molecular weight of the free base form of alogliptin). Thus, specific dosage amounts that may be used include, but are not limited to 10 mg, 12.5 mg, 20 mg, 25 mg, 50 mg, 75 mg and 100 mg of alogliptin per day. Alogliptin may be administered in its free base form or as a pharmaceutically acceptable salt.

Saxagliptin may be administered to a patient at a daily dose of between 2.5 mg/day and 100 mg/day, optionally between 2.5 mg and 50 mg. Specific dosage amounts that may be used include, but are not limited to 2.5 mg, 5 mg, 10 mg, 15 mg, 20 mg, 30 mg, 40 mg, 50 mg and 100 mg of saxagliptin per day. Typical dosage strengths of the dual combination of saxagliptin/metformin are 2.5/500 mg and 2.5/1000 mg.

A special embodiment of the DPP-4 inhibitors of this invention refers to those orally administered DPP-4 inhibitors which are therapeutically efficacious at low dose levels, e.g. at oral dose levels <100 mg or <70 mg per patient per day, preferably <50 mg, more preferably <30 mg or <20 mg, even more preferably from 1 mg to 10 mg, particularly from 1 mg to 5 mg (more particularly 5 mg), per patient per day (if required, divided into 1 to 4 single doses, particularly 1 or 2 single doses, which may be of the same size, preferentially, administered orally once- or twice daily (more preferentially once-daily), advantageously, administered at any time of day, with or without food. Thus, for example, the daily oral amount 5 mg BI 1356 can be given in an once daily dosing regimen (i.e. 5 mg BI 1356 once daily) or in a twice daily dosing regimen (i.e. 2.5 mg BI 1356 twice daily), at any time of day, with or without food.

The GLP-1 receptor agonist is typically administered by subcutaneous injection, e.g. ranging from thrice daily, twice daily, once daily to once weekly injection. Suitable doses and dosage forms of the GLP-1 receptor agonist may be determined by a person skilled in the art. For example, exenatide is administered twice daily by subcutaneous injection (Byetta, 5-30 µg, particularly 5-20 µg, preferably 5-10 µg, specific dosage strengths are 5 or 10 µg) before a main meal.

Exenatide LAR is administered once weekly by subcutaneous injection (0.1-3 mg, particularly 0.5 mg to 2.0 mg, specific dosage strengths are 0.8 mg or 2.0 mg).

Liraglutide is administered once daily by subcutaneous injection (Victoza, 0.5-3 mg, particularly 0.5 mg to 2 mg, specific dosage strengths are 0.6 mg, 0.9 mg, 1.2 mg or 1.8 mg).

Taspoglutide is administered once weekly by subcutaneous injection (1-30 mg, specific dosage strengths are 1 mg, 8 mg, 10 mg, 20 mg or 30 mg).

Semaglutide is administered once weekly by subcutaneous injection (0.1-1.6 mg).

Albiglutide is administered once weekly by subcutaneous injection (4-30 mg, specific dosage strengths are 4 mg, 15 mg or 30 mg).

Lixisenatide is administered once daily by subcutaneous injection (10-20 µg, specific dosage strengths are 10 µg, 15 µg or 20 µg).

Dulaglutide is administered once weekly by subcutaneous injection (0.25-3 mg, specific dosage strengths are 0.25 mg, 0.5 mg, 0.75 mg, 1.0 mg, 1.5 mg, 2.0 mg or 3.0 mg).

Besides delivery by injection, other routes of administration of GLP-1 receptor agonists may be contemplated, for example, GLP-1 receptor agonists for use in combination therapy within the meaning of this invention also include, without being limited, such ones which are suited and/or formulated for oral delivery, continuous (subcutaneous) delivery, pulmonary (e.g. via inhalation) or nasal delivery, or transdermal delivery (e.g. via patch), with subcutaneous injection being preferred.

The dosage of the active ingredients in the combinations and compositions in accordance with the present invention may be varied, although the amount of the active ingredients shall be such that a suitable dosage form is obtained. Hence, the selected dosage and the selected dosage form shall depend on the desired therapeutic effect, the route of administration and the duration of the treatment. Suitable dosage ranges for the combination are from the maximal tolerated dose for the single agent to lower doses, e.g. to one tenth of the maximal tolerated dose.

A particularly preferred DPP-4 inhibitor to be emphasized within the meaning of this invention is 1-[(4-methyl-quinazolin-2-yl)methyl]-3-methyl-7-(2-butyn-1-yl)-8-(3-(R)-amino-piperidin-1-yl)-xanthine (also known as BI 1356 or linagliptin). BI 1356 exhibits high potency, 24 h duration of action, and a wide therapeutic window. In patients with type 2 diabetes receiving multiple oral doses of 1, 2.5, 5 or 10 mg of BI 1356 once daily for 12 days, BI 1356 shows favourable pharmacodynamic and pharmacokinetic profile (see e.g. Table i below) with rapid attainment of steady state (e.g. reaching steady state plasma levels (>90% of the pre-dose plasma concentration on Day 13) between second and fifth day of treatment in all dose groups), little accumulation (e.g. with a mean accumulation ratio $R_{A,AUC} \leq 1.4$ with doses above 1 mg) and preserving a long-lasting effect on DPP-4 inhibition (e.g. with almost complete (>90%) DPP-4 inhibition at the 5 mg and 10 mg dose levels, i.e. 92.3 and 97.3% inhibition at steady state, respectively, and >80% inhibition over a 24 h interval after drug intake), as well as significant decrease in 2 h postprandial blood glucose excursions by ≥80% (already on Day 1) in doses ≥2.5 mg, and with the cumulative amount of unchanged parent compound excreted in urine on Day 1 being below 1% of the administered dose and increasing to not more than about 3-6% on Day 12 (renal clearance $CL_{R,ss}$ is from about 14 to about 70 mL/min for the administered oral doses, e.g. for the 5 mg dose renal clearance is about 70 ml/min). In people with type 2 diabetes BI 1356 shows a placebo-like safety and tolerability. With low doses of about ≥5 mg, BI 1356 acts as a true once-daily oral drug with a full 24 h duration of DPP-4 inhibition. At therapeutic oral dose levels, BI 1356 is mainly excreted via the liver and only to a minor extent (about <7% of the administered oral dose) via the kidney. BI 1356 is primarily excreted unchanged via the bile. The fraction of BI 1356 eliminated via the kidneys increases only very slightly over time and with increasing dose, so that there will likely be no need to modify the dose of BI 1356 based on the patients' renal function. The non-renal elimination of BI 1356 in combination with its low accumulation potential and broad safety margin may be of significant benefit in a patient population that has a high prevalence of renal insufficiency and diabetic nephropathy.

TABLE I

Geometric mean (gMean) and geometric coefficient of variation (gCV) of pharmacokinetic parameters of BI 1356 at steady state (Day 12)

| Parameter | 1 mg gMean (gCV) | 2.5 mg gMean (gCV) | 5 mg gMean (gCV) | 10 mg gMean (gCV) |
|---|---|---|---|---|
| $AUC_{0-24}$ [nmol · h/L] | 40.2 (39.7) | 85.3 (22.7) | 118 (16.0) | 161 (15.7) |
| $AUC_{T,ss}$ [nmol · h/L] | 81.7 (28.3) | 117 (16.3) | 158 (10.1) | 190 (17.4) |
| $C_{max}$ [nmol/L] | 3.13 (43.2) | 5.25 (24.5) | 8.32 (42.4) | 9.69 (29.8) |
| $C_{max,ss}$ [nmol/L] | 4.53 (29.0) | 6.58 (23.0) | 11.1 (21.7) | 13.6 (29.6) |
| $t_{max}$* [h] | 1.50 [1.00-3.00] | 2.00 [1.00-3.00] | 1.75 [0.92-6.02] | 2.00 [1.50-6.00] |
| $t_{max,ss}$* [h] | 1.48 [1.00-3.00] | 1.42 [1.00-3.00] | 1.53 [1.00-3.00] | 1.34 [0.50-3.00] |
| $T_{1/2,ss}$ [h] | 121 (21.3) | 113 (10.2) | 131 (17.4) | 130 (11.7) |
| Accumulation $t_{1/2}$ [h] | 23.9 (44.0) | 12.5 (18.2) | 11.4 (37.4) | 8.59 (81.2) |
| $R_{A,Cmax}$ | 1.44 (25.6) | 1.25 (10.6) | 1.33 (30.0) | 1.40 (47.7) |
| $R_{A,AUC}$ | 2.03 (30.7) | 1.37 (8.2) | 1.33 (15.0) | 1.18 (23.4) |
| $fe_{0-24}$ [%] | NC | 0.139 (51.2) | 0.453 (125) | 0.919 (115) |
| $fe_{T,ss}$ [%] | 3.34 (38.3) | 3.06 (45.1) | 6.27 (42.2) | 3.22 (34.2) |
| $CL_{R,ss}$ [mL/min] | 14.0 (24.2) | 23.1 (39.3) | 70 (35.0) | 59.5 (22.5) |

*median and range [min-max]
NC not calculated as most values below lower limit of quantification As different metabolic functional disorders often occur simultaneously, it is quite often indicated to combine a number of different active principles with one another. Thus, depending on the functional disorders diagnosed, improved treatment outcomes may be obtained if a DPP-4 inhibitor is combined with active substances customary for the respective disorders, such as e.g. one or more active substances selected from among the other antidiabetic substances, especially active substances that lower the blood sugar level or the lipid level in the blood, raise the HDL level in the blood, lower blood pressure or are indicated in the treatment of atherosclerosis or obesity.

The DPP-4 inhibitors mentioned above—besides their use in mono-therapy—may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; mitiglinide, thiazolidinediones such as rosiglitazone and pioglitazone; PPAR gamma modulators such as metaglidases; PPAR-gamma agonists such as mitoglitazone, INT-131, balaglitazone or rivoglitazone; PPAR-gamma antagonists; PPAR-gamma/alpha modulators such as tesaglitazar, muraglitazar, aleglitazar, indeglitazar and KRP297; PPAR-gamma/alpha/delta modulators such as e.g. lobeglitazone; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as SMT3-receptor-agonists and GPR119, such as the GPR119 agonists 5-ethyl-2-{4-[4-(4-tetrazol-1-yl-phenoxymethyl)-thiazol-2-yl]-piperidin-1-yl}-pyrimidine or 5-[1-(3-isopropyl-[1,2,4]oxadiazol-5-yl)-piperidin-4-ylmethoxy]-2-(4-methanesulfonyl-phenyl)-pyridine; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin degludec, insulin tregopil, insulin zinc suspension and insulin glargin; Gastric inhibitory Peptide (GIP); amylin and amylin analogues (e.g. pramlintide or davalintide); GLP-1 and GLP-1 analogues such as Exendin-4, e.g. exenatide, exenatide LAR, liraglutide, taspoglutide, lixisenatide (AVE-0010), LY-2428757 (a PEGylated version of GLP-1), dulaglutide (LY-2189265), semaglutide or albiglutide; SGLT2-inhibitors such as e.g. dapagliflozin, sergliflozin (KGT-1251), atigliflozin, canagliflozin or (1S)-1,5-anhydro-1-[3-(1-benzothiophen-2-ylmethyl)-4-fluorophenyl]-D-glucitol, ipragliflozin, tofogliflozin, luseogliflozin; inhibitors of protein tyrosine-phosphatase (e.g. trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976) or of serine/threonine kinases; glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors; KV 1.3 channel inhibitors; GPR40 modulators such as e.g. [(3S)-6-({2',6'-dimethyl-4'-[3-(methylsulfonyl)propoxy]biphenyl-3-yl}methoxy)-2,3-dihydro-1-benzofuran-3-yl]acetic acid; SCD-1 inhibitors; CCR-2 antagonists; dopamine receptor agonists (bromocriptine mesylate [Cycloset]); 4-(3-(2,6-dimethylbenzyloxy)phenyl)-4-oxobutanoic acid; sirtuin stimulants; and other DPP IV inhibitors.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

For children 10 to 16 years of age, the recommended starting dose of metformin is 500 mg given once daily. If this dose fails to produce adequate results, the dose may be increased to 500 mg twice daily. Further increases may be made in increments of 500 mg weekly to a maximum daily dose of 2000 mg, given in divided doses (e.g. 2 or 3 divided doses). Metformin may be administered with food to decrease nausea.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (or up to 40 mg divided twice) a day (typical dosage strengths are 5 and 10 mg), or extended-release glibenclamide in doses from 5 to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

A dual combination of glibenclamide/metformin is usually given in doses from 1.25/250 once daily to 10/1000 mg twice daily. (typical dosage strengths are 1.25/250, 2.5/500 and 5/500 mg).

A dual combination of glipizide/metformin is usually given in doses from 2.5/250 to 10/1000 mg twice daily (typical dosage strengths are 2.5/250, 2.5/500 and 5/500 mg).

A dual combination of glimepiride/metformin is usually given in doses from 1/250 to 4/1000 mg twice daily.

A dual combination of rosiglitazone/glimepiride is usually given in doses from 4/1 once or twice daily to 4/2 mg twice daily (typical dosage strengths are 4/1, 4/2, 4/4, 8/2 and 8/4 mg).

A dual combination of pioglitazone/glimepiride is usually given in doses from 30/2 to 30/4 mg once daily (typical dosage strengths are 30/4 and 45/4 mg).

A dual combination of rosiglitazone/metformin is usually given in doses from 1/500 to 4/1000 mg twice daily (typical dosage strengths are 1/500, 2/500, 4/500, 2/1000 and 4/1000 mg).

A dual combination of pioglitazone/metformin is usually given in doses from 15/500 once or twice daily to 15/850 mg thrice daily (typical dosage strengths are 15/500 and 15/850 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

Acarbose is usually given in doses from 25 to 100 mg with meals. Miglitol is usually given in doses from 25 to 100 mg with meals.

Examples of combination partners that lower the lipid level in the blood are HMG-CoA-reductase inhibitors such as simvastatin, atorvastatin, lovastatin, fluvastatin, pravastatin, pitavastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists such as e.g. {4-[(R)-2-ethoxy-3-(4-trifluoromethyl-phenoxy)-propylsulfanyl]-2-methyl-phenoxy}-acetic acid; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 (dalcetrapib) or compound 12 from WO 2007/005572 (anacetrapib); LDL receptor modulators; MTP inhibitors (e.g. lomitapide); and ApoB100 antisense RNA.

A dosage of atorvastatin is usually from 1 mg to 40 mg or 10 mg to 80 mg once a day.

Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan, azilsartan and eprosartan.

A dosage of telmisartan is usually from 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apolipoprotein A-I.

Examples of combination partners for the treatment of obesity are sibutramine; tetrahydrolipstatin (orlistat); alizyme (cetilistat); dexfenfluramine; axokine; cannabinoid receptor 1 antagonists such as the CB1 antagonist rimonobant; MCH-1 receptor antagonists; MC4 receptor agonists; NPY5 as well as NPY2 antagonists (e.g. velneperit); beta3-AR agonists such as SB-418790 and AD-9677; 5HT2c receptor agonists such as APD 356 (lorcaserin); myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine; as well as the dual combinations bupropion/naltrexone, bupropion/zonisamide, topiramate/phentermine and pramlintide/metreleptin.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

The aim of this study is to evaluate the effects of repeated administration of a GLP-1 receptor agonist, such as e.g. exenatide (30 µg/kg/day sc) by subcutaneous minipump for 10 or 28 days and exenatide (30 µg/kg/day sc) for 10 days followed by vehicle or BI 1356 (3 mg/kg po) given orally on body weight in dietary-induced obese (DIO) female Wistar rats (ie in an animal model of obesity). BI 1356 is a novel compound with potential for the treatment of obesity/diabetes. All experimental procedures concerning the use of laboratory animals are carried out under a Home Office Certificate of Designation.

Methodology:

Obesity is induced-in female Wistar rats for 20 weeks by giving the animals free access to powdered high fat diet (VRF1 plus 20% lard), ground chocolate, ground peanuts and tap water at all times. Two weeks before the start of the baseline readings, animals are housed singly in polypropylene cages with wire grid floors to enable the food intake of each rat to be recorded. Following a 5-day baseline period, osmotic minipumps (2ML2) delivering either vehicle or exenatide are implanted subcutaneously (sc) under anaesthetic. The surgery is performed over two days and therefore the study was divided into two arms (staggered by one day) and the data pooled. On day 11, the osmotic minipumps are removed from all animals and replaced with a new pump (2ML4) containing vehicle or exenatide for 10 days. In addition animals are treated orally with either vehicle (0.5% Natrosol) or BI 1356 and body weight is recorded daily as shown in FIG. 1.

When the osmotic mini-pumps start to emerge through the wound clips, animals are re-clipped on one occasion per animal only. Rats are removed from the feeding laboratory for approximately 30 min and the wound resealed under brief (~10 min) anaesthesia. If the wound re-opened the rat is terminated.

Results: Exenatide leads to significant weight loss during the first 11 days. When the animals receive vehicle+vehicle from day 11 on, they gain weight again. However, the animals treated further with the DPP 4 inhibitor BI 1356 stabilize their body weight at the new weight level and are significantly lighter than the vehicle-treated control animals (see FIG. 1).

Specific surgical procedures: Animals are anaesthetised using gaseous anaesthesia (isoflurane). Specifically, anaesthesia is induced with isoflurane (5%), $O_2$ (2 l/min), $N_2O$ (2 l/min). During this time the implant site is shaved. All surgery will use aseptic technique. During surgery, anaesthesia is maintained with isoflurane at 2%, with $O_2$ (1 l/min) and $N_2O$ (1 l/min). The incision is sited at the flank, and a pocket of suitable size is created and the pump inserted. Pumps are filled with vehicle or exenatide shortly before implantation. The wound is sealed by the use of one or more wound clips (VetTech Solutions). Betadine spray and Opsite dressing are applied to the wound. Immediately post surgery, the $N_2O$ gas stream is removed and $O_2$ increased to a flow rate of 2 l/min. After approximately 1 min, isoflurane is turned off. Once animals begin to show signs of recovery (e.g. faster breathing rate, tail and/or limb movement) they are placed into the home cage on a heat mat with a heat lamp present. Animals are carefully monitored for up to 2 h following surgery and until they are fully recovered. As soon as the rats recover from the anaesthetic they have free access to food and water.

Figure 2:
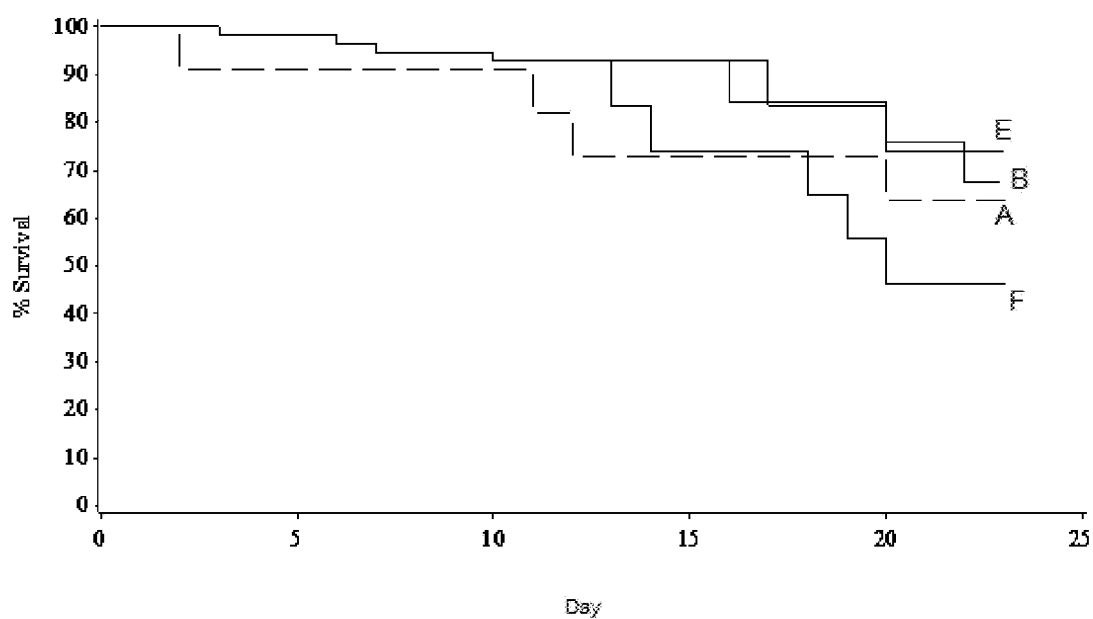
FIG. 2 shows survival plots of animals after about 22-23 days treatment for vehicle treated animals (A), exenatide+vehicle-treated animals (B), exenatide+BI 1356-treated animals (E), and exenatide-treated animals (F).

Exenatide-treated animals show higher incidence for skin alterations, which lead often to euthanization of the respective animals. Linagliptin-treated animals show better survival (see FIG. 2, e.g. after about 22-23 days treatment, vehicle treated animals (A) show about 65% survival, exenatide+vehicle-treated animals (B) show about 67% survival, exenatide+BI 1356-treated animals (E) show about 75% survival, and exenatide-treated animals (F) show about 45% survival).

Figure 3:
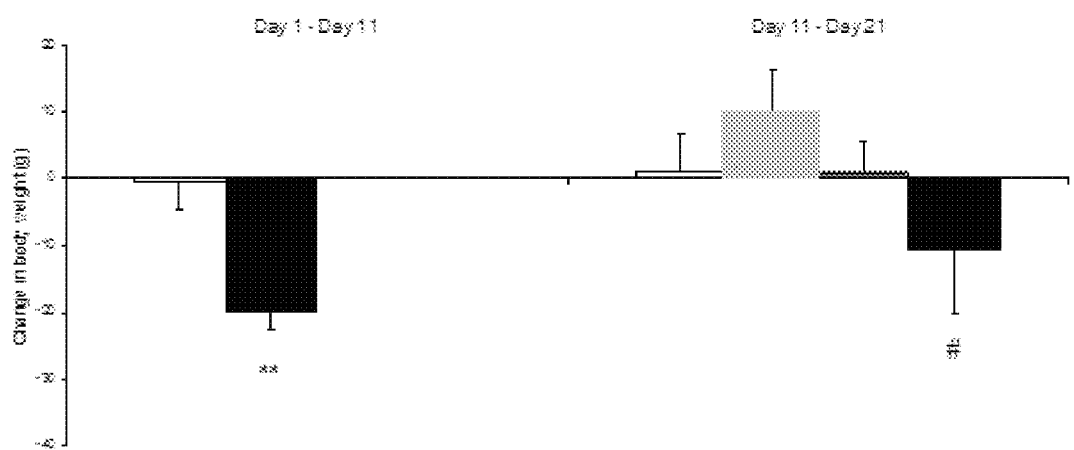
FIG. 3 shows the mean change in body weight of obese female Wistar rats treated with Vehicle (-□-); Exatinide 30 μg/kg/day (Day 1-10)+Vehicle (from Day 11) (-▩-); Exatinide 30 μg/kg/day (Day 1-10)+BI 1356 3 mg/kg po (from Day 11) (-▩-); and Exatinide 30 μg/kg/day (-■-). Day 1-11 data with exenatide are pooled and include all data for animals treated with exenatide over this period). Means are adjusted for differences between the body weights of the different treatment groups at baseline (Day 1). SEMs are calculated from the residuals of the statistical model. the vehicle control group were by the multiple t test. Significant differences from vehicle control: *$p<0.05$; **$p<0.01$. Significant differences from Exenatide 30 μg/kg/day (Day 1-10)+vehicle s.c. and p.o. (from Day 11): #$p=0.07$ (multiple t test).

As shown in FIG. 3, linagliptin attenuates rebound of body weight (including body fat) gain following discontinuation of GLP-1R agonist (e.g. exendin-4) treatment. Results are mean change in body weight of obese female Wistar rats treated with exenatide for either a 10 or 21 day period (n=5-11; Day 1-11 data with exenatide are pooled and include all data for animals treated with exenatide over this period). Means are adjusted for differences between the body weights of the different treatment groups at baseline (Day 1). SEMs are calculated from the residuals of the statistical model. On day 11, the mini-pump was removed and replaced with a second mini-pump. Animals treated with exenatide for 10 days were switched to vehicle treatment for the rest of the study. The change in body weight of animals treated with the DPP-4 inhibitor, linagliptin (3 mg/kg po), on exenatide withdrawal are illustrated on the figure (first bar from right: Exenatide; second bar from right: Exenatide followed by Linagliptin; third bar from right: Exenatide followed by Vehicle). Multiple comparisons versus the vehicle control group were by the multiple t test. Significant differences from vehicle control: *$p<0.05$; **$p<0.01$. Significant differences from Exenatide 30 µg/kg/day (Day 1-10)+vehicle s.c. and p.o. (from Day 11): #$p=0.07$ (multiple t test).

Figure 4A:
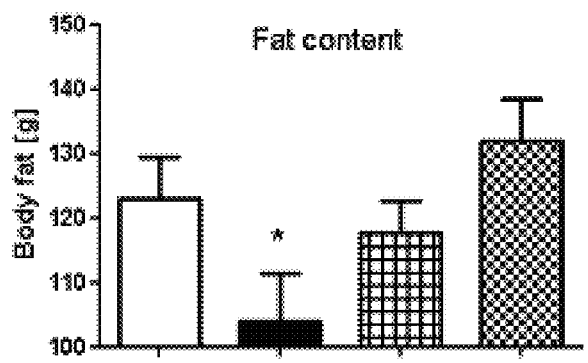
FIGS. 4A-4C shows the effects of GLP-1R agonist (e.g. exendin-4) cessation and replacement with linagliptin on body fat (FIG. 4A), protein content (FIG. 4B) and water content (4C) for rats treated with Vehicle (-□-); Exatinide 30 μg/kg/day (Day 1-10)+Vehicle (from Day 11) (- -); Exatinide 30 μg/kg/day (Day 1-10)+linagliptin 3 mg/kg po (from Day 11) (-▤-); and Exatinide 30 μg/kg/day (Day 1-10)+Exatinide 30 μg/kg/day (from Day 11) (-▨-).
Figure 4B:
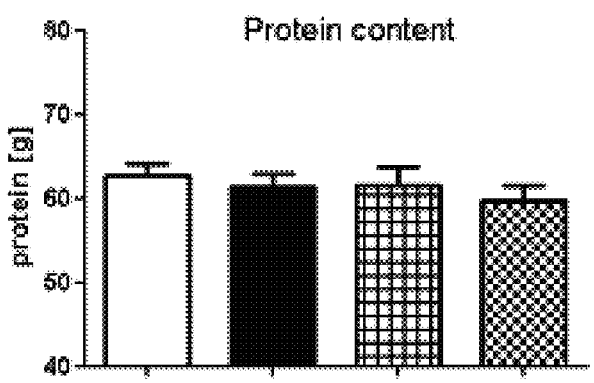
Figure 4C:
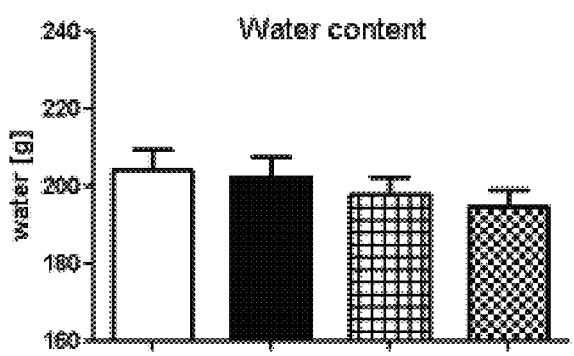

As shown in FIGS. 4A=4C, GLP-1R agonist (e.g. exendin-4) cessation and replacement with linagliptin prevents body fat weight regain.

TABLE (a)

Carcass composition and final body weight (prior to tissue dissection) of animals at the study conclusion

| | Water (g) | | Fat (g) | | | Protein (g) | | Final Weight (g) | |
|---|---|---|---|---|---|---|---|---|---|
| | Mean | SEM | Mean | SEM | | Mean | SEM | Mean | SEM |
| Vehicle (Day 1-10) + Vehicle (from Day 11); Vehicle po from Day 11 | 204.2 | 5.3 | 123.0 | 6.5 | | 62.7 | 1.4 | 438.2 | 4.6 |
| Exenatide 30 µg/kg/day (Day 1-10) + Vehicle (from Day 11); Vehicle po from Day 11 | 194.6 | 4.3 | 132.0 | 6.3 | | 59.7 | 1.8 | 424.4 | 4.5 |
| Exenatide 30 µg/kg/day (Day 1-10) + Vehicle (from Day 11); linagliptin 3 mg/kg po from Day 11 | 198.0 | 4.4 | 117.6 | 5.0 | | 61.6 | 2.1 | 419.1 | 5.7 |
| Exenatide 30 µg/kg/day (Day 1-10) + Exenatide (30 µg/kg/day from Day 11); | 202.1 | 5.2 | 103.9 | 7.5 | *$$ | 61.4 | 1.5 | 410.5 | 8.3 |

Table (a): Table detailing the carcass composition and final body weight (prior to tissue dissection) of animals at the study conclusion, n = 6-10. Data are adjusted for differences between treatment groups in body weight at baseline (Day 1). SEMs are calculated from the residuals of the statistical model.
Comparisons against the control group were by the multiple t test:
*p < 0.05.
Comparisons against the vehicle-treated exenatide withdrawal group by multiple t test:
$$p < 0.01.

The effect of linagliptin (BI 1356, 3 mg/kg po, once daily for 28 days) either alone or in combination with a low dose of exenatide (3 µg/kg/day sc) on body weight, carcass composition and relevant plasma markers of obese female Wistar rats fed a high-fat cafeteria diet (DIO) rats for approximately 20 weeks is assessed. Linagliptin has no effect on body weight, daily food intake, plasma glucose, insulin or carcass fat in DIO rats compared to vehicle-treated controls and does not augment the effect of a low dose of exenatide (delivered via a subcutaneously implanted osmotic minipump), when dosed in combination.

In a follow on study (21 days duration), a high dose of exenatide (30 µg/kg/day sc) is shown to reduce body weight (6%; p<0.001) and body fat (16% p<0.05) in DIO rats compared to vehicle-treated controls. Carcass protein (p=0.8) and water (p=0.7) are not affected. In DIO rats where the osmotic minipump delivering exenatide is removed (Day 10) and replaced by an osmotic minipump delivering saline, weight regain is observed such that the body weight of these animals is not significantly different to controls (p=0.239) after 21 days. In contrast, linagliptin (3 mg/kg po) reduces weight regain after withdrawal of exenatide such that a significant difference from controls is evident (p<0.05). This weight regain is characterized principally by fat deposition and linagliptin-treated animals put on 10.6% less fat than vehicle-treated counterparts during exenatide withdrawal (p=0.07). In this context, please see also FIG. 3, FIGS. 4A-4C and Table (a).

These data demonstrate that linagliptin has no weight reducing effect per se in untreated DIO rats or in DIO rats treated with exenatide but in DIO rats where weight loss is induced by a high dose of a GLP-1 receptor agonist or exenatide and then withdrawn, linagliptin reduces or delays subsequent weight regain. Linagliptin can therefore be used in controlling weight rebound during intermittent courses of treatment with a GLP-1 receptor agonist or exenatide.

Diabetic patients may switch from one treatment to another in an effort to avoid unpleasant side effects like nausea that are frequently reported with a GLP-1 receptor agonist or exenatide treatment.

In conclusion, the present study demonstrates that linagliptin (BI 1356) does not significantly alter body weight, food intake or carcass composition in an established and validated animal model of obesity, i.e. drug-naïve female Wistar rats allowed continuous exposure to a simplified three-component cafeteria diet in order to develop marked obesity, insulin resistance (e.g. hyperinsulinaemia) and/or impaired glucose tolerance.

Although exhibiting dietary-induced obesity, the rats used in the present studies do not exhibit a diabetic phenotype and, accordingly, their plasma glucose and HbA1c levels are within a normal range.

Accordingly, the present data shows that treatment with linagliptin is a useful strategy for the weight-neutral treatment of diabetes since, in contrast to other drug classes (e.g. thiazolidinediones, sulphonylureas, insulin etc,) linagliptin is unlikely to promote weight gain, a major causative factor in the development of diabetes.

Further, the present data are the first to demonstrate that dietary-induced obese rats treated with exenatide lose weight compared to vehicle controls but put this weight back on once withdrawn from the drug. Importantly, this body weight gain does not increase beyond the level of vehicle-treated controls and there is evidence that this weight gain, especially the increase in fat, may be reduced by treatment with linagliptin. Thus, the present invention provides a treatment regimen comprising inducing initial weight loss, e.g. via GLP-1 receptor agonism, and subsequently being replaced by or switching to a DPP-4 inhibitor (preferably linagliptin) treatment, which is favourable for reducing, preventing or delaying subsequent weight regain after weight loss, particularly the concomitant increase in body fat.

It is further shown that also the direct combination of linagliptin and low dose of a GLP-1 receptor agonist (exenatide) has a positive effect on body fat which is greater than for the respective single agents (see Table (b)).

TABLE (b)

Effect of linagliptin and exenatide combination on plasma parameters and body composition in DIO rats

| | Day 29 Pump treatment (SC) | | | | |
|---|---|---|---|---|---|
| | Vehicle | Exenatide (3 µg/kg/day) | Exenatide (30 µg/kg/day) | Vehicle | Exenatide (3 µg/kg/day) |
| | | | Oral treatment | | |
| | Vehicle | Vehicle | Vehicle | Linagliptin (3 mg/kg PO) | Linagliptin (3 mg/kg PO) |
| Glucose (mM) | 8.14 ± 0.33 | 8.06 ± 0.31 | 7.70 ± 0.21 | 8.72 ± 0.22 | 8.51 ± 0.21 |
| Insulin (ng/mL) | 2.12 ± 0.34 | 1.89 ± 0.32 | 1.61 ± 0.64 | 1.82 ± 0.36 | 1.89 ± 0.31 |
| Leptin (ng/mL) | 26.7 ± 2.6 | 20.5 ± 2.3 | 14.4 ± 1.2$^c$ *** | 23.9 ± 2.5 | 21.1 ± 1.6 |
| GLP-1 (pM) | 3.67 ± 1.1 | 3.52 ± 0.3 | 4.58 ± 0.5 | 5.72 ± 0.9$^b$ | 5.44 ± 1.3$^{b,d}$ |
| Carcass Protein (g) | 60.8 ± 4.6 | 55.6 ± 5.2 | 54.3 ± 3.5 | 63.8 ± 4.0 | 63.7 ± 5.1 |
| Carcass Water (g) | 206.8 ± 5.9 | 209.9 ± 7.7 | 207.5 ± 3.5 | 212.6 ± 3.4 | 213.6 ± 3.8 |
| Carcass Fat (g) | 161.1 ± 5.9 | 144.7 ± 10.0 | 127.3 ± 9.3 ** | 151.1 ± 7.3 | 139.5 ± 7.1$^a$ |

Table (b): Data are mean ± SEM (n = 7-10). Multiple comparisons vs. vehicle are by Williams' test for groups treated solely with exenatide, and the multiple t test for all other groups:
$^a$P = 0.050,
$^b$P < 0.05,
$^c$P < 0.001.
$^d$P < 0.05 from the exenatide (3 µg/kg/day) group.
GLP-1, glucagon-like peptide-1.

These data show that adding linagliptin to a GLP-1 receptor agonist (e.g. exenatide) provides a dose-sparing effect on the use of the GLP-1 receptor agonist.

In a further study the efficacy of chronic treatment with linagliptin on body weight, total body fat, intra-myocellular fat, and hepatic fat in a non-diabetic model of diet induced obesity (DIO) in comparison to the appetite suppressant sibutramine is investigated:

Rats are fed a high-fat diet for 3 months and received either vehicle, linagliptin (10 mg/kg), or sibutramine (5 mg/kg) for 6 additional weeks, while continuing the high-fat diet. Magnetic resonance spectroscopy (MRS) analysis of total body fat, muscle fat, and liver fat is performed before treatment and at the end of the study.

Sibutramine causes a significant reduction of body weight (-12%) versus control, whereas linagliptin has no significant effect (-3%). Total body fat is also significantly reduced by sibutramine (-12%), whereas linagliptin-treated animals show no significant reduction (-5%). However, linagliptin and sibutramine result both in a potent reduction of intramyocellular fat (−24% and −34%, respectively). In addition, treatment with linagliptin results in a profound decrease of hepatic fat (-39%), whereas the effect of sibutramine (-30%) does not reach significance (see Table (c)). Thus, linagliptin is weight neutral but improves intra-myocellular and hepatic lipid accumulation.

TABLE (c)

Effect of linagliptin on body weight total body fat, liver fat and intramyocellular fat

| | Body weight | | Total body fat | | Liver fat | | Intra-myocellular fat | |
|---|---|---|---|---|---|---|---|---|
| | % contr. | % baseli. | % contr. | % baseli. | % contr. | % baseli. | % contr. | % baseli. |
| Control | — | +15% | — | +11% | — | +27% | — | +23% |
| | | p = 0.016 | | p = 0.001 | | p = 0.09 | | p = 0.49 |
| Linagliptin | -3% | +12% | -5% | +5% | -39% | -30% | -36% | -24% |
| | p = 0.56 | p = 0.001 | p = 0.27 | p = 0.06 | p = 0.022 | p = 0.05 | p = 0.14 | p = 0.039 |
| Sibutramine | -12% | +1% | -12% | -0.4% | -30% | -29% | -55% | -34% |
| | p = 0.018 | p = 0.64 | p = 0.008 | p = 0.86 | p = 0.13 | p = 0.12 | p = 0.037 | p = 0.007 |

In conclusion, linagliptin treatment provokes a potent reduction of intramyocellular lipids and hepatic fat, which are both independent of weight loss. The effects of sibutramine on muscular and hepatic fat are attributed mainly to the known weight reduction induced by this compound.

---

---

The invention claimed is:

1. A method for treating or reducing the risk of skin necrosis associated or induced by (a) injections by a needle or syringe pierced through the skin or (b) infusions, in a patient in need thereof, said method comprising orally administering linagliptin to said patient.

2. The method according to claim 1, wherein the skin necrosis is from subcutaneous injection of a GLP-1 receptor agonist, insulin, or insulin analog.

* * * * *